(12) United States Patent
Murakami et al.

(10) Patent No.: US 7,524,284 B2
(45) Date of Patent: Apr. 28, 2009

(54) ENDOSCOPY SYSTEM

(75) Inventors: Kazushi Murakami, Hino (JP);
 Takaaki Komiya, Akiruno (JP); Yoshio Onuki, Hachioji (JP); Takehiro Nishiie, Akishima (JP); Yasuhito Kura, Hachioji (JP); Hiroaki Ichikawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 569 days.

(21) Appl. No.: 11/347,876

(22) Filed: Feb. 6, 2006

(65) Prior Publication Data

US 2007/0185377 A1 Aug. 9, 2007

(51) Int. Cl.
 *A61B 1/00* (2006.01)
(52) U.S. Cl. .......................... 600/106; 600/104; 606/46
(58) Field of Classification Search ......... 600/104–106, 600/114; 606/46
 See application file for complete search history.

(56) References Cited

U.S. PATENT DOCUMENTS

| | | | | |
|---|---|---|---|---|
| 5,431,645 | A * | 7/1995 | Smith et al. ..................... | 606/1 |
| 5,596,991 | A * | 1/1997 | Tanaka ....................... | 600/459 |
| 5,695,491 | A | 12/1997 | Silverstein | |
| 5,827,175 | A * | 10/1998 | Tanaka ....................... | 600/104 |
| 5,971,929 | A * | 10/1999 | Sakamoto et al. ........... | 600/462 |
| 6,092,722 | A | 7/2000 | Heinrichs et al. | |
| 6,764,439 | B2 * | 7/2004 | Schaaf et al. ................ | 600/106 |
| 7,048,684 | B2 * | 5/2006 | Parasher et al. ............. | 600/104 |
| 2002/0087048 | A1 * | 7/2002 | Brock et al. ................. | 600/114 |
| 2002/0107538 | A1 * | 8/2002 | Shibata et al. .............. | 606/169 |
| 2005/0192475 | A1 * | 9/2005 | Okada ........................ | 600/106 |
| 2005/0267327 | A1 | 12/2005 | Iizuka et al. | |
| 2006/0258095 | A1 | 11/2006 | Kaji et al. | |
| 2008/0039685 | A1 * | 2/2008 | Komiya et al. .............. | 600/106 |

FOREIGN PATENT DOCUMENTS

| | | |
|---|---|---|
| JP | 57-190541 | 11/1982 |
| JP | 2000-000207 | 1/2000 |
| WO | WO 03/013372 A2 | 2/2003 |
| WO | WO 2005/070282 A1 | 8/2005 |

\* cited by examiner

*Primary Examiner*—John P Leubecker
*Assistant Examiner*—Victoria W Chen
(74) *Attorney, Agent, or Firm*—Scully, Scott, Murphy & Presser, P.C.

(57) ABSTRACT

An endoscopy system includes: a motor-driven operating device that an operation section of an accessory is attachable to, the operating device operating the operation section in a motor-driven manner, the accessory having an accessory insertion section to be introduced into a body cavity through an insertion section of an endoscope; a motor-driven forward/backward moving device, arranged in an operation section of the endoscope, for moving the accessory insertion section forward or backward in a motor-driven manner; a control device electrically connected to the motor-driven forward/backward moving device and the motor-driven operating device, the control device including a control unit for outputting control signals to the forward/backward moving device and the operating device and a memory unit for storing one or more treatment operation programs corresponding to accessories to be mounted on the motor-driven forward/backward moving device; and an operation instructing device electrically connected to the control device, the operation instructing device including a first operation instructing unit for outputting a first instruction signal corresponding to the operation of a manual operation unit and a second operation instructing unit for outputting a second instruction signal.

7 Claims, 16 Drawing Sheets

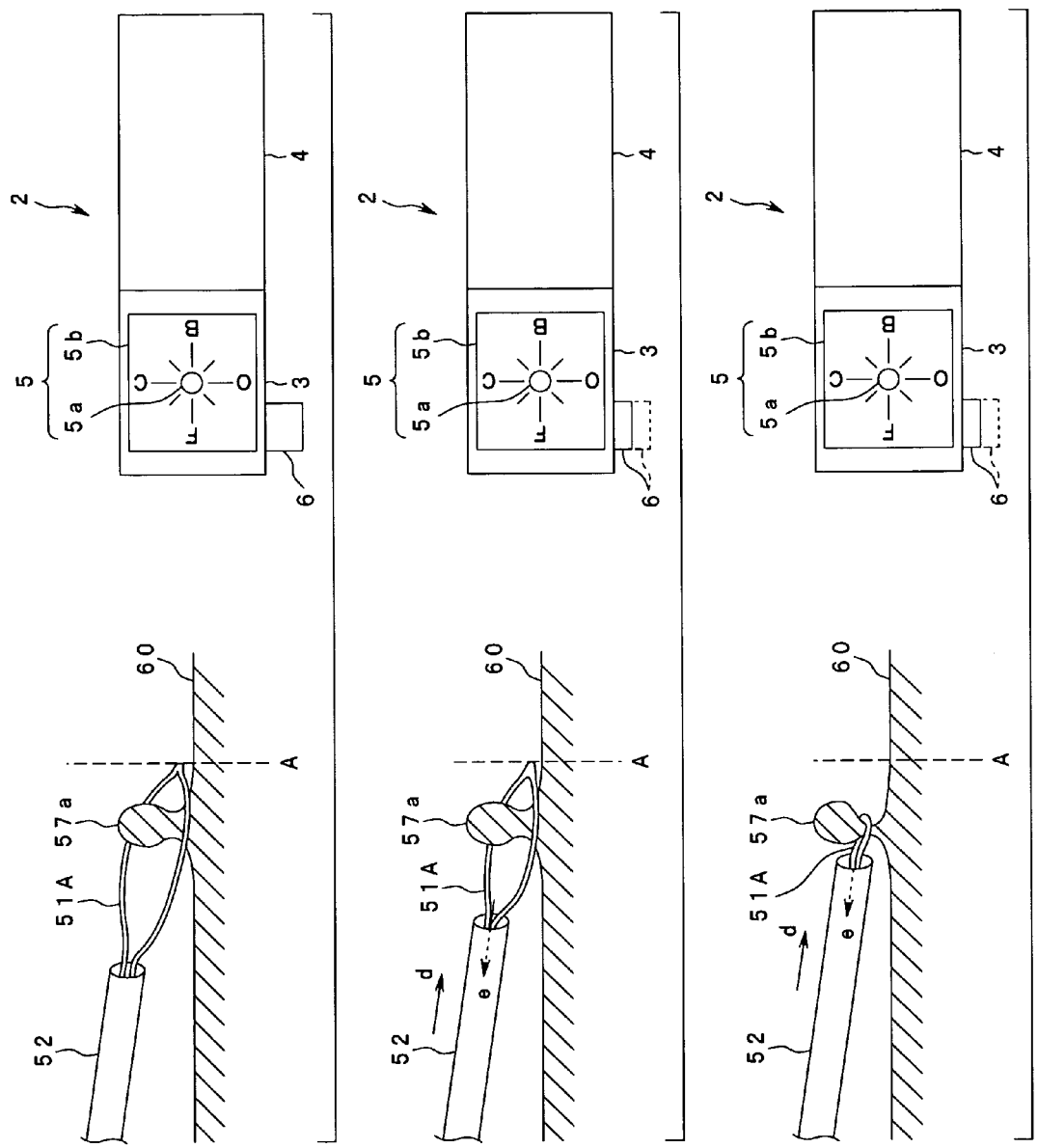

ENDOSCOPY SYSTEM

BACKGROUND OF THE INVENTION

1. Field of the Invention

The present invention relates to an endoscopy system including an endoscope, accessories used in combination with the endoscope, and an endoscopic operation assist device capable of easily performing various operations using the accessories.

2. Description of Related Art

Recently, endoscopes have been widely used in the medical field. An endoscope includes an elongated insertion section and an operation section provided at the proximal end of the insertion section. Generally, a bendable portion is provided at the distal end of the elongated insertion section. The operation section includes a knob to bend the bendable portion and various switches for various operations of endoscopic functions.

In the endoscope used in the medical field, to observe an organ in a body cavity, the insertion section is inserted into the body cavity of a subject. The endoscope is capable of performing various treatments using accessories introduced into the body cavity through an accessory channel in the insertion section.

To insert an accessory into the accessory channel of the endoscope, an operator holds a sheath, serving as an insertion section of the accessory, and manually inserts the sheath into the accessory channel. However, this manual insertion takes time. Further, in order to prevent the sheath having a length of, e.g., 2 m, from buckling and keep the sheath from contact with an unclean area, considerable care has to be exercised in inserting the sheath. The insertion is complicated and difficult for the operator.

To solve the above-described problems, e.g., Japanese Unexamined Patent Application Publication No. 57-190541 discloses an endoscope that enables a sheath of an accessory to be mechanically inserted into an accessory channel.

Japanese Unexamined Patent Application Publication No. 2000-207 discloses an endoscopic accessory inserting/removing apparatus that enables an accessory to be mechanically inserted and further enables a treating member of an accessory to be mechanically operated on the basis of an instruction output from a foot switch.

In the above cases, an operator operates the treating member to actually perform treatment. Accordingly, a result of treatment depends on the skill of the operator. In other words, there is a large gap between the skill of an inexperienced doctor and that of a richly experienced one.

SUMMARY OF THE INVENTION

An endoscopy system includes an operating device, a forward/backward moving device, a control device, and an operation instructing device. An operation section of an accessory is attachable to the operating device. Each accessory has an accessory insertion section to be introduced into a body cavity through an insertion section of an endoscope. The operating device operates the operation section in a motor-driven manner. The forward/backward moving device is arranged in an operation section of the endoscope. The forward/backward moving device moves the accessory insertion section forward or backward in a motor-driven manner. The control device is electrically connected to the forward/backward moving device and the operating device. The control device includes a control unit for outputting control signals to the forward/backward moving device and the operating device. In addition, the control device includes a memory unit for storing one or more treatment operation programs corresponding to accessories to be mounted on the operating device. The operation instructing device is electrically connected to the control device. The operation instructing device includes a manual operation unit, a first operation instructing unit for outputting a first instruction signal corresponding to the operation of the manual operation unit, and a second operation instructing unit for outputting a second instruction signal. When receiving the first instruction signal, the control device outputs a control signal corresponding to the first instruction signal to at least one of the forward/backward moving device and the operating device. On the other hand, when receiving the second instruction signal, the control device executes the treatment operation program stored in the memory unit. The control device outputs a control signal, based on the operation according to the treatment operation program, to at least one of the forward/backward moving device and the operating device.

The above and other objects, features and advantages of the invention will become more clearly understood from the following description referring to the accompanying drawings.

BRIEF DESCRIPTION OF THE DRAWINGS

FIG. 13A is a diagram explaining a state before a diathermic snare is operated by the operation instructing device;

FIG. 13B is a diagram explaining a state where the diathermic snare is operated in the programmed operation;

FIG. 13C is a diagram explaining a state where the operation of the diathermic snare is completed in the programmed operation;

DETAILED DESCRIPTION OF PREFERRED EMBODIMENTS

Embodiments of the present invention will now be described below with reference to the drawings.

A first embodiment of the present invention will now be described with reference to FIGS. 1 to 12.

Figure 1:
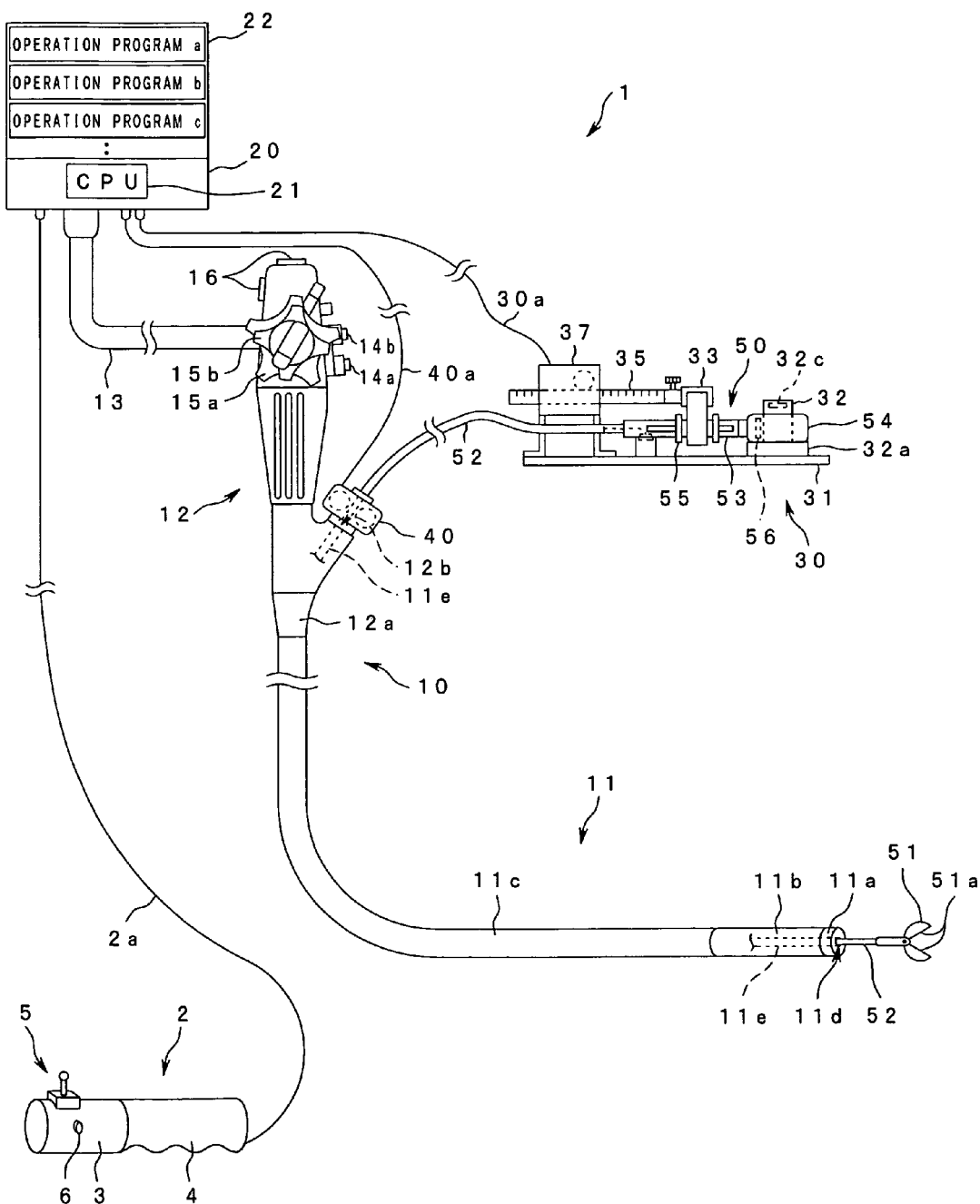
FIG. 1 is a diagram explaining the entire structure of an endoscopy system according to a first embodiment.

Referring to FIG. 1, an endoscopy system 1 primarily includes an operation instructing device 2, an endoscope 10, a control device 20, serving as a light source and a video processor, a motor-driven accessory operating device (hereinafter, referred to as a motor-driven operating device) 30, serving as an operating device, and a motor-driven forward/backward accessory insertion section moving device (hereinbelow, referred to as a motor-driven forward/backward moving device) 40, serving as a forward/backward moving device. According to the present embodiment, the operation instructing device 2, the control device 20, the motor-driven operating device 30, and the motor-driven forward/backward moving device 40 constitute an endoscopic operation assist apparatus.

The control device 20 includes a CPU 21, serving as a control unit, and a memory device 22, serving as a memory unit, such as a hard disk. The memory device 22 stores treatment operation programs a, b, c, . . . which correspond to respective accessories. Each program is used during treatment using the corresponding accessory introduced into a body cavity through an accessory channel, which will be described later, in the endoscope 10. The control device 20 is connected to a liquid crystal display (not shown) for displaying endoscopic images and the like.

For example, the memory device 22 stores the operation program a for biopsy forceps, the operation program b for a diathermic snare, the operation program c for a cannula, the operation program d for basket forceps, and the like.

The endoscope 10 includes an insertion section 11, an operation section 12, and a universal cord 13. The operation section 12 also serves as a grasping portion provided at the proximal end of the insertion section 11. The universal cord 13 extends from one side of the operation section 12. The proximal end of the universal cord 13 is connected to the control device 20.

The insertion section 11 includes a rigid distal end portion 11a, a bendable portion 11b, and a flexible tube 11c which are arranged in that order from the distal end of the insertion section 11. The operation section 12 includes an anti-buckling member 12a connected to the proximal end of the flexible tube 11c. The operation section 12 includes an air/water supply button 14a for air/water supply, a suction button 14b for suction, knobs 15a and 15b to operate the bendable portion 11b, and various switches 16 for controlling an endoscopic image which is captured by image pickup means, such as a CCD, provided at the distal end portion 11a and is displayed on a screen of the display, and so on.

The endoscope 10 has an accessory channel 11e communicating with an accessory opening 12b and a distal end opening 11d formed at the distal end portion 11a.

The operation instructing device 2 is electrically connected to the control device 20 via a signal cable 2a through which a plurality of signal lines are inserted.

The motor-driven operating device 30 is electrically connected to the control device 20 via an electric cable 30a through which a plurality of signal lines are inserted. In the motor-driven operating device 30, a handle 53 as an operating member of an accessory, e.g., biopsy forceps 50, is set.

The motor-driven forward/backward moving device 40 is attached to an accessory mounting member 12c having the accessory opening 12b in the endoscope 10. The motor-driven forward/backward moving device 40 is electrically connected to the control device 20 via an electric cable 40a through which signal lines are inserted. A sheath 52, serving as an accessory insertion section, constituting the biopsy forceps 50 is introduced into or withdrawn from the accessory channel 11e by the motor-driven forward/backward moving device 40. In other words, the sheath 52 of the biopsy forceps 50 is moved forward or backward in the accessory channel 11e by the motor-driven forward/backward moving device 40.

A tissue pickup member 51, serving as a treating member, is disposed at the distal end of the sheath 52 of the biopsy forceps 50. The tissue pickup member 51 includes a pair of biopsy cups that are closable. An operating wire (not shown) is inserted through the sheath 52 of the biopsy forceps 50. The operating wire is moved forward or backward by operating the handle 53. The forward or backward movement of the operating wire switches the tissue pickup member 51 between an open state and a closed state. The handle 53 includes a pickup ring 54 and a slider 55. The pickup ring 54 includes a hole into which, e.g., the thumb of a user is inserted. The slider 55 has a pair of flanges on which the middle and ring fingers of the user are arranged. The pickup ring 54 includes, e.g., a contactless IC chip (hereinbelow, referred to as an IC chip) 56 constituting an accessory information unit of an RFID system serving as accessory specifying means. The IC chip 56 stores treating member information indicative of the kind of accessory. The biopsy cups, constituting the tissue pickup member 51, respectively have a tissue pressure sensor (hereinafter, abbreviated to a sensor) 51a. A signal line (not shown) extends from each sensor 51a. Each signal line is inserted through the sheath 52 and the other end thereof is connected to an electric contact point (refer to reference numeral 57 in FIG. 9) arranged in the slider 55.

The operation instructing device 2 will now be described with reference to FIGS. 1 to 4.

Figure 2:
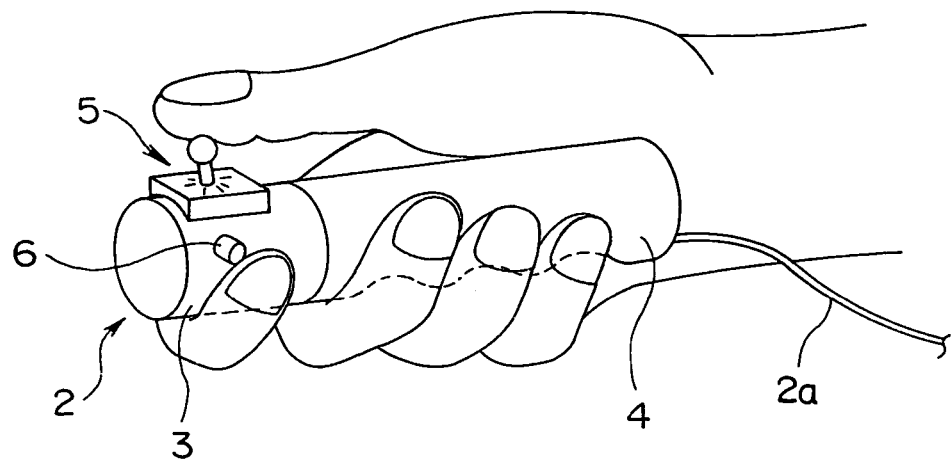
FIG. 2 is a diagram showing an operation instructing device held by an operator's hand.
Figure 3:
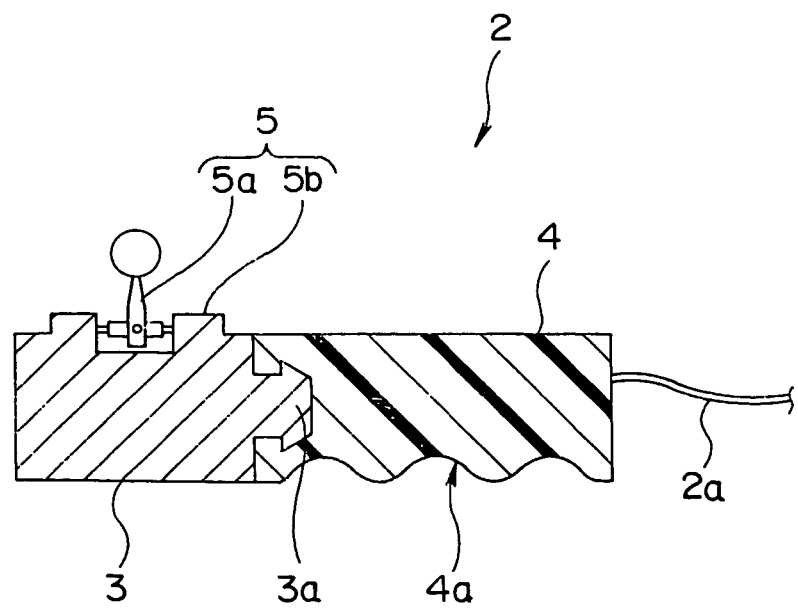
FIG. 3 is a sectional view of the operation instructing device.

Referring to FIGS. 1 and 2, the operation instructing device 2 includes a rigid body portion 3 which is, e.g., substantially cylindrical and a grip member 4 connected to the body portion 3. The grip member 4 is made of, e.g., an elastic material. The signal cable 2a extends from the proximal end of the grip member 4. A fitting projection 3a projects from the center of the proximal end surface of the body portion 3. The fitting projection 3a is fitted into a fitting hole formed at the distal end surface of the grip member 4, so that the body portion 3 is integrated with the grip member 4.

In the side surface of the body portion 3, a manual operation instructing unit (hereinafter, referred to as a manual operation unit) 5, serving as a first operation instructing unit, and a program operation instructing unit (hereinafter, referred to as a program operation unit) 6, serving as a second operation instructing unit, are arranged.

On the other hand, the grip member 4 includes a grip portion 4a having projections and depressions. The grip portion 4a is arranged on the side surface such that the grip portion 4a and the manual operation unit 5 of the body portion 3 face in opposite directions. When an operator grasps the grip portion 4a, the operator can securely grasp the operation instructing device 2.

In the operation instructing device 2 with the above-described structure, in the following description, the distal end of the body portion 3 will be referred to as the distal end of the operation instructing device 2, the proximal end of the grip member 4 will be referred to as the proximal end thereof, the side on which the manual operation unit 5 in the body portion 3 is arranged will be referred to as the upper portion thereof, and the side on which the grip portion 4a of the grip member 4 is formed will be referred to as the lower portion thereof.

The manual operation unit 5 includes a so-called joystick type control lever 5a which is an origin return switch operable in two axial directions. The control lever 5a is supported by a control-lever supporting portion 5b. In the case of using the biopsy forceps 50 as an accessory, the control lever 5a outputs an operation signal, serving as a first instruction signal, to operate the tissue pickup member 51 inserted into a body cavity through the accessory channel 11e.

Specifically, when the control lever 5a is tilted toward the distal end, an operation signal to forwardly move the sheath 52 is output to the CPU 21. When the control lever 5a is tilted toward the proximal end, an operation signal to backwardly move the sheath 52 is output to the CPU 21. When the control lever 5a is tilted to the left relative to the distal end as viewed from above, an operation signal to open the tissue pickup member 51 is output to the CPU 21. When the control lever 5a is tilted to the right relative to the distal end as viewed from above, an operation signal to close the tissue pickup member 51 is output to the CPU 21.

Figure 4:
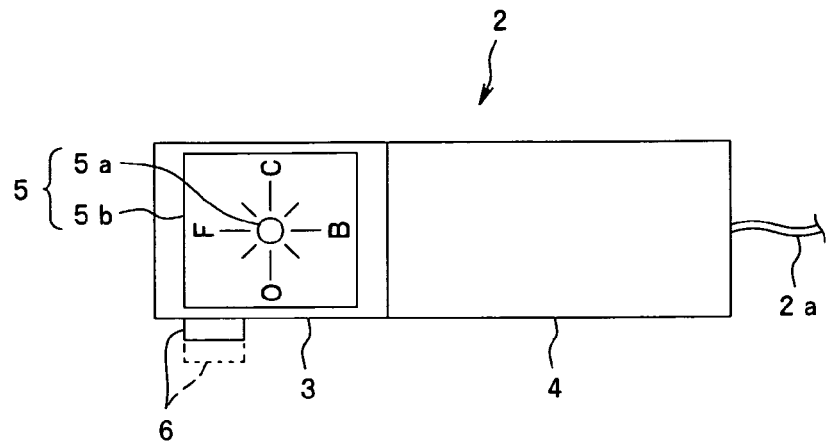
FIG. 4 is a top view of the operation instructing device.

On the upper surface of the control-lever supporting portion 5b of the manual operation unit 5, reference marks indicating operation instructions for the biopsy forceps 50 corresponding to the tilt directions of the control lever 5a may be arranged. FIG. 4 shows an example of the reference marks, i.e., characters. A reference mark "FORWARD (F)" is printed at the distal end of the control-lever supporting portion 5b. A reference mark "BACKWARD (B)" is printed at the proximal end. An reference mark "OPEN (O)" is printed on the left relative to the distal end as viewed from above, i.e., at the lower end in the diagram. An reference mark "CLOSE (C)" is printed on the right relative to the distal end as viewed from above, i.e., at the upper end in the diagram.

As shown in FIG. 4, in the structure in which the manual operation unit 5 is arranged on the upper portion of the body portion 3, the program operation unit 6 is disposed in the side surface on the left relative to the distal end as viewed from above (i.e., the lower portion in the diagram) such that the position of the program operation unit 6 is deviated from that of the manual operation unit 5 in the circumferential direction by 90 degrees. The program operation unit 6 is, e.g., a push type switch. After being pushed, the switch is held in a position shown by the solid line. When the switch is protruded as shown by the broken line, the switch is in the OFF state. When the switch is pushed as shown by the solid line, the switch is in the ON state, i.e., the switch outputs an automatic operation instruction signal, serving as a second instruction signal, to the CPU 21 of the control device 20.

Figure 5:
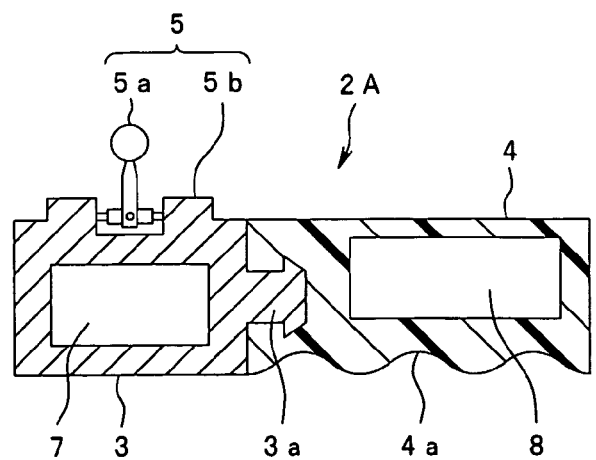
FIG. 5 is a sectional view explaining a modification of the operation instructing device.

To return the program operation unit 6 to the original state, the program operation unit 6 is further pushed. The program operation unit 6 may be a push type switch designed in such a manner that after being pushed, the switch is returned to the original state. According to the present embodiment, the operation instructing device 2 is connected to the control device 20 via the signal cable 2a, i.e., the operation instructing device 2 is a wired type. The operation instructing device 2 is not limited to the wired type. As shown in FIG. 5, a wireless type operation instructing device 2A may be used. The operation instructing device 2A includes a transmitter 7 built in, e.g., the body portion 3 and a power supply battery 8 in the grip member 4. Therefore, the operation instructing device 2A transmits instruction signals output from the manual operation unit 5 and the program operation unit 6 to the control device 20 through the transmitter 7 using power supplied from the battery 8. In this structure, therefore, the control device 20 includes a receiver (not shown) for receiving instruction signals from the transmitter 7.

Figure 6:
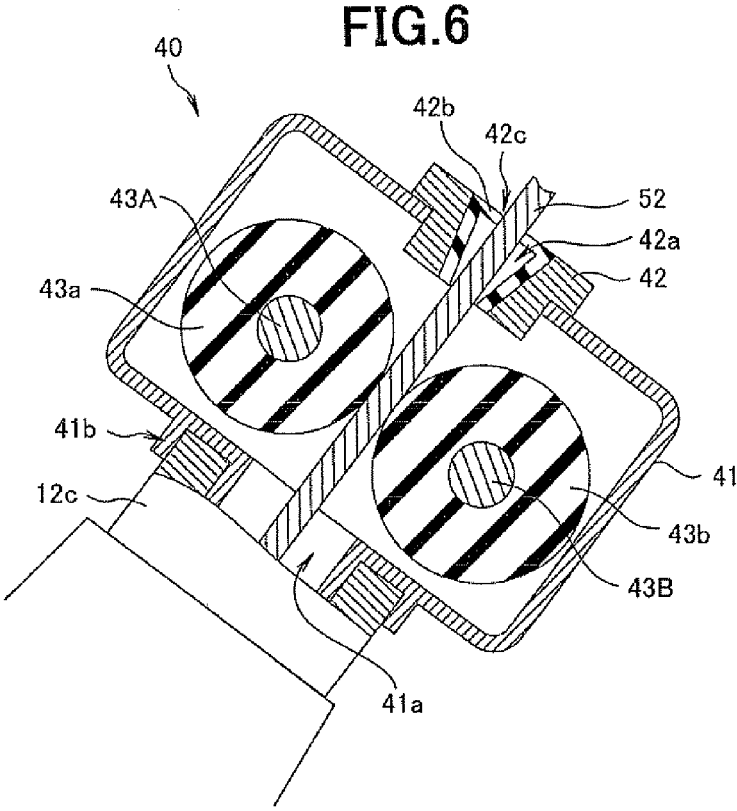
FIG. 6 is a longitudinal sectional view showing the internal structure of a motor-driven forward/backward moving device.
Figure 7:
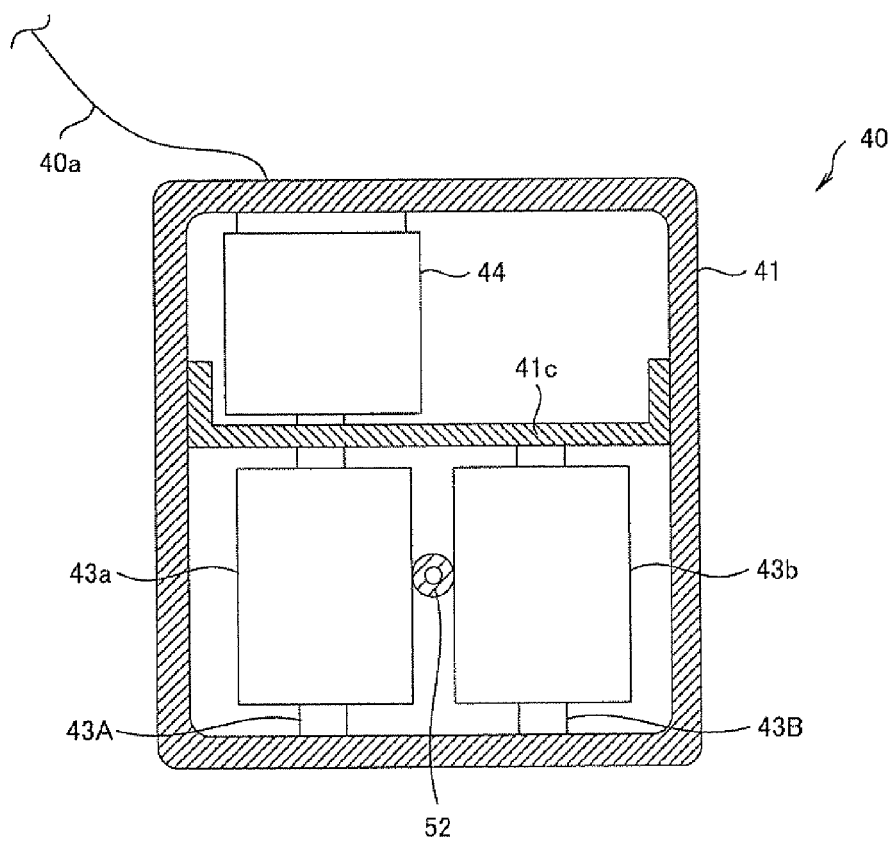
FIG. 7 is a transverse sectional view of the internal structure of the motor-driven forward/backward moving device.

The motor-driven forward/backward moving device 40 will now be described with reference to FIGS. 1, 6, and 7.

The motor-driven forward/backward moving device 40 includes a housing 41 and two rollers 43a and 43b that are rotatably arranged in the housing 41. An accessory insertion member 42 through which the sheath 52 of the biopsy forceps 50 is inserted is arranged in one of opposed surfaces of the housing 41. The accessory insertion member 42 has a through hole 42a. A forceps tap 42b, made of an elastic material, is arranged in the through hole 42a. A slit 42c to which the sheath 52 is inserted is formed in the forceps tap 42b. In the other surface of the housing 41, a sheath insertion hole 41a through which the sheath 52 inserted through the slit 42c passes is formed. A scope fixing member 41b to connect and fix the housing 41 to the accessory mounting member 12c is arranged in the vicinity of the sheath insertion hole 41a. The scope fixing member 41b is air-tightly connected to the accessory mounting member 12c.

For example, in a case where air is supplied with the endoscope 10 to inflate a body cavity in order to easily observe the body cavity, when the sheath 52 of the biopsy forceps 50 is withdrawn by the motor-driven forward/backward moving device 40 attached to the accessory mounting member 12c, a reduction in pressure in the body cavity can be prevented.

Each of the two rollers 43a and 43b, arranged in the housing 41, is made of an elastic resin material. The rollers 43a and 43b are integrally fixed to rotating shafts 43A and 43B, respectively. The outer surface of the sheath 52 inserted through the slit 42c is pressed and held in the nip between the rollers 43a and 43b. The rotating shaft 43A is a driving shaft that is rotated by a motor 44 disposed in the housing 41. On the other hand, the rotating shaft 43B is a driven shaft that is rotatably arranged in the housing 41.

In this structure, when the motor 44 is driven while the sheath 52 is being held between the rollers 43a and 43b, the drive shaft 43A is rotated. Then, rotating the roller 43a forwardly or backwardly moves the sheath 52 held between the rollers 43a and 43b. In other words., the sheath 52 is moved forward or backward in the accessory channel 11e by driving the motor 44.

The rotating shafts 43A and 43B are rotatably supported by one side wall of the housing 41 and a support plate 41c such that the rotating shafts 43A and 43B are parallel to each other and the surfaces of the rollers 43a and 43b fixed to the rotating shafts 43A and 43B are spaced at a predetermined distance from each other.

Figure 8:
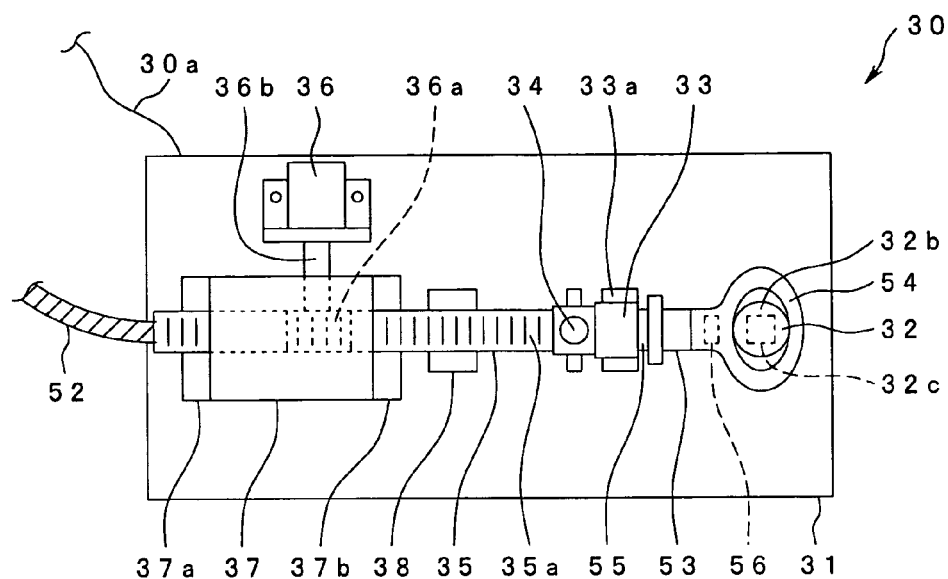
FIG. 8 is a top view of a motor-driven operating device.

The motor-driven operating device 30 will now be described with reference to FIGS. 1, 8, and 9.

The motor-driven operating device 30 includes a plate-shaped base 31. A ring retainer 32, a holding box 37, and a mount 38 are fixed to the base 31. The holding box 37 is fixed to the base 31 through a pair of fixing members 37a and 37b. The holding box 37 holds a rack 35 having linear teeth 35a such that the rack 35 is movable forward or backward. In the holding box 37, a pinion gear 36a that engages with the linear teeth 35a of the rack 35 is arranged. The pinion gear 36a is fixed to a motor shaft 36b of a motor 36. Therefore, when the motor 36 is rotated while the pinion gear 36a engages with the linear teeth 35a formed in the rack 35, the pinion gear 36a fixed to the motor shaft 36b is rotated, so that the rack 35 is moved forward or backward.

A slider retainer 33 having a holding member 33a is attached to one end of the rack 35 through a fastening screw 34. The holding member 33a constituting the slider retainer 33 is arranged between parts of the slider 55 constituting the handle 53. Specifically, the holding member 33a holds a middle part between the pair of flanges arranged on the slider 55 so as to pinch the part.

The ring retainer 32 includes a ring base 32a and a protruding portion 32b. The ring base 32a is fixed to the base 31. The protruding portion 32b is inserted into the hole of the pickup ring 54 constituting the handle 53. The protruding portion 32b includes an accessory information reading unit (hereinafter, referred to as a reader/writer) 32c, serving as an information reading unit for reading accessory information stored in the IC chip 56. The reader/writer 32c and the IC chip 56 constitute the RFID system.

Lowering the pickup ring 54 so that the protruding portion 32b may be inserted into the hole of the pickup ring 54 retains the handle 53 integrally on the motor-driven operating device 30. In this instance, the reader/writer 32c reads information stored in the IC chip 56. The read treating member information is output to the CPU 21 through a signal line (not shown) in the electric cable 30a. Consequently, the CPU 21 recognizes the type of accessory.

When the pickup ring 54 is arranged on the protruding portion 32b in a predetermined state, a plane of the pickup ring 54 is come into contact with the ring base 32a. In this arrangement, part of the handle 53 is arranged on the mount 38. Accordingly, the handle 53 of the biopsy forceps 50 is spaced from and parallel to the base 31. The mount 38 includes an electric connection point 38a to be electrically connected to the electric contact point 57. Therefore, when the handle 53 is mounted on the mount 38, the electric contact point 57 is electrically connected to the electric connection point 38a. In other words, a detection signal output from each sensor 51a is output to the CPU 21 through a signal line (not shown), the electric contact point 57, the electric connection point 38a, and a signal line (not shown) in the electric cable 30a.

In this structure, driving of the motor 36 moves the rack 35, so that the slider 55 held by the slider retainer 33 attached to the rack 35 is moved forward or backward along the axis of the handle 53. Then, the operating wire is moved in association with the forward or backward movement of the slider 55, thus opening or closing the tissue pickup member 51 constituting the biopsy forceps 50.

The protruding portion 32b constituting the ring retainer 32 is formed such that the outer diameter thereof is substantially identical to the inner diameter of the hole of the pickup ring 54. Therefore, the handle 53 is securely held by the ring retainer 32.

The outer diameter of the protruding portion 32b of the ring retainer 32 may be slightly smaller than the inner diameter of the hole of the pickup ring 54. In this case, the periphery of the protruding portion 32b is covered with an elastic tube. Consequently, the handle 53 can be securely held by the ring retainer 32.

In the endoscopy system 1 with the above-described structure, when the control lever 5a of the manual operation unit 5 is tilted toward the distal end or the proximal end, a first instruction signal is output to the CPU 21 of the control device 20 through the signal cable 2a. In response to the instruction signal, the CPU 21 outputs a control signal through the electric cable 40a in order to rotate the motor 44 in the motor-driven forward/backward moving device 40 in accordance with an operation signal. Thus, the motor 44 is rotated in the direction desired by the operator. Consequently, the driving roller 43a is rotated. Then, the sheath 52 pressed between the rollers 43a and 43b is moved forward or backward in association with the rotation, so that the tissue pickup member 51 is moved forward or backward.

In other words, the operator tilts the control lever 5a of the manual operation unit 5 toward the distal end or proximal end, thereby freely controlling the tissue pickup member 51, i.e., projecting the tissue pickup member 51 from the distal end portion 11a of the insertion section 11 toward target tissue or moving back the tissue pickup member 51 in the direction to the distal end portion 11a.

On the other hand, when the control lever 5a of the manual operation unit 5 is tilted to the left or right relative to the distal end of the manual operation unit 5 as viewed from above, a first instruction signal is output to the CPU 21 of the control device 20 through the signal cable 2a. In response to the instruction signal, the CPU 21 outputs a control signal through the electric cable 30a in order to rotate the motor 36 in the motor-driven operating device 30 in accordance with an operation signal. Thus, the motor 36 is rotated in the direction desired by the operator. Consequently, the rack 35 having the linear teeth 35a engaging with the pinion gear 36a is moved forward or backward in association with the rotation of the pinion gear 36a provided for the motor shaft 36b.

Since the slider 55 is held by the slider retainer 33 coupled to the rack 35, the slider 55 is moved forward or backward along the axis of the handle 53. Thus, the movement of the slider 55 moves the operating wire forward or backward, thus opening or closing the tissue pickup member 51.

In other words, the operator tilts the control lever 5a of the manual operation unit 5 to the left or right, thereby freely operating the tissue pickup member 51 so as to open or close the member 51.

In the manual operation unit 5, when the operator tilts the control lever 5a in the direction between the adjacent reference marks among the marks indicating the distal-end direction, proximal-end direction, the left, and the right, the operator can simultaneously move the tissue pickup member 51 forward or backward and open or close the tissue pickup member 51.

Each of the forward or backward moving speed and opening or closing speed depends on the angle of tilt of the control lever 5a of the manual operation unit 5. Specifically, as the angle formed between the tilted control lever 5a and its initial position becomes larger, each of the forward or backward moving speed and the opening or closing speed is increased.

On the other hand, when the program operation unit 6 is pushed, a second instruction signal is output to the CPU 21 of the control device 20 through the signal cable 2a. In response to the instruction signal, the CPU 21 executes the program corresponding to accessory information read by the reader/writer 32c, i.e., the biopsy-forceps operation program for operating the biopsy forceps 50 among the programs stored in the memory device 22 on the basis of the accessory information. In the programmed operation, the CPU 21 outputs a control signal through the electric cable 40a in order to rotate the motor 44 in the motor-driven forward/backward moving device 40 in a predetermined direction. Alternatively, the CPU 21 outputs a control signal through the electric cable 30a in order to rotate the motor 36 in the motor-driven operating device 30 in a predetermined direction. Thus, the tissue pickup member 51 is moved forward or backward and is opened or closed in the programmed operation.

The operation of the endoscopy system 1 with the above-described structure will now be explained.

Before using the endoscopy system 1 in a surgical operation, medical staffs prepare as follows.

Figure 9:
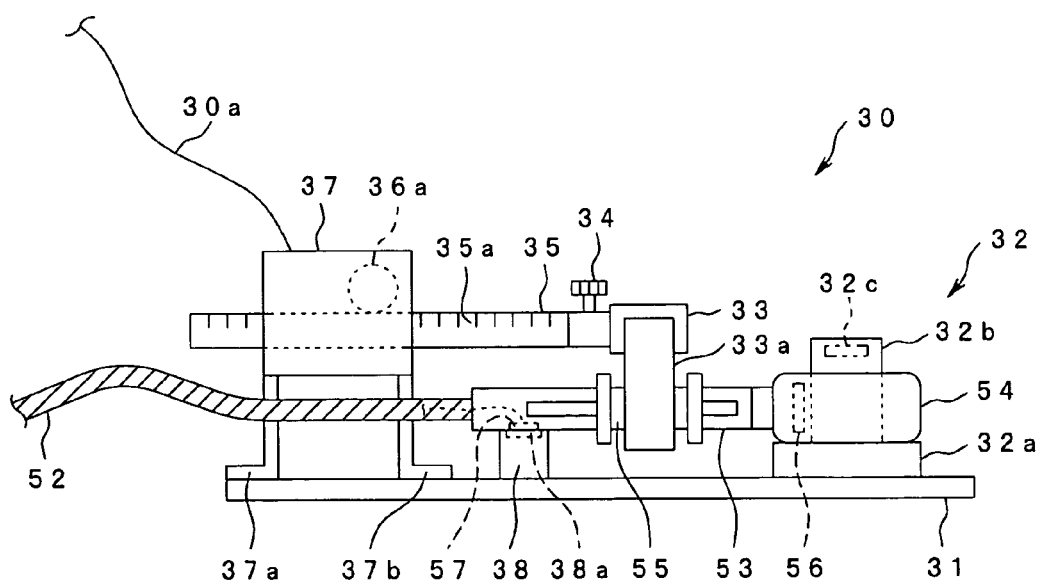
FIG. 9 is a side view of the motor-driven operating device.

A worker attaches the handle 53 of an accessory to be used in the surgical operation, e.g., the biopsy forceps 50 to the motor-driven operating device 30 (refer to FIG. 9). The slider retainer 33, which is detached from the rack 35 in this instance, is mounted on the slider 55 constituting the handle 53 of the biopsy forceps 50. Then, the pickup ring 54 of the handle 53 is set to the ring retainer 32. At that time, the worker sets the pickup ring 54 such that a plane of the pickup ring 54 is in contact with the ring base 32a of the ring retainer 32 and arranges part of the handle 53 on the mount 38. After that, as shown in FIG. 9, the worker couples the slider retainer 33 to the rack 35 via the fastening screw 34.

In addition, the worker attaches the motor-driven forward/backward moving device 40 to the accessory mounting member 12c of the endoscope 10 (refer to FIG. 6) and then inserts the sheath 52 into the accessory channel 11e of the endoscope 10 through the motor-driven forward/backward moving device 40 such that the tissue pickup member 51 of the biopsy forceps 50 is first inserted and the sheath 52 of the biopsy forceps 50 is pressed between the rollers 43a and 43b.

The worker may previously introduce the sheath 52 into the accessory channel 11e of the endoscope 10 manually and arrange the tissue pickup member 51 in front of the distal end of the insertion section 11.

Further, the worker connects the signal cable 2a extending from the operation instructing device 2 to the control device 20 and confirms whether each of the universal cord 13 and the electric cables 30a and 40a is connected to the control device 20 in a predetermined connection state.

After completion of preparation, the medical staff turns on the control device 20. Then, accessory information stored in the IC chip 56 provided in the handle 53 is read by the reader/writer 32c arranged in the protruding portion 32b. The read information is output to the CPU 21.

Figure 10:
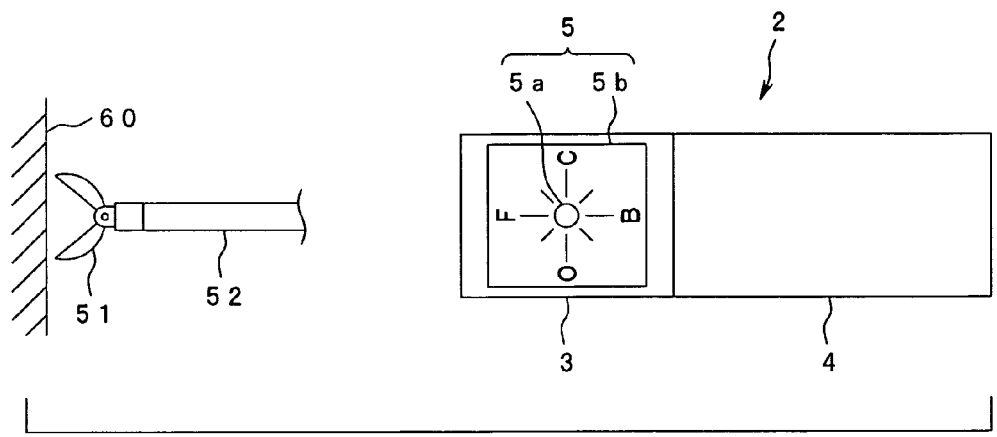
FIG. 10 is a diagram explaining a state before biopsy forceps are operated by the operation instructing device.

Subsequently, an operator inserts the insertion section 11 of the endoscope 10 into the body cavity of a subject toward a target region while observing endoscopic images. While confirming endoscopic images on the screen, the operator performs the inserting operation and the bending operation of bending the bendable portion 11b, thus allowing the distal end portion 11a of the insertion section 11 to face the tissue in the target region so that treatment can be easily performed. In this instance, as shown in FIG. 10, the tissue pickup member 51 of the biopsy forceps 50 reaches in the vicinity of tissue 60. After that, while observing endoscopic images, the operator controls the biopsy forceps 50. At that time, the operator holds the operation instructing device 2 as shown in FIG. 2.

In this instance, when the operator selects the control lever 5a of the manual operation unit 5, a first instruction signal is output to the CPU 21. Consequently, the tissue pickup member 51 is controlled in response to the operation by the operator's finger.

Figure 11:
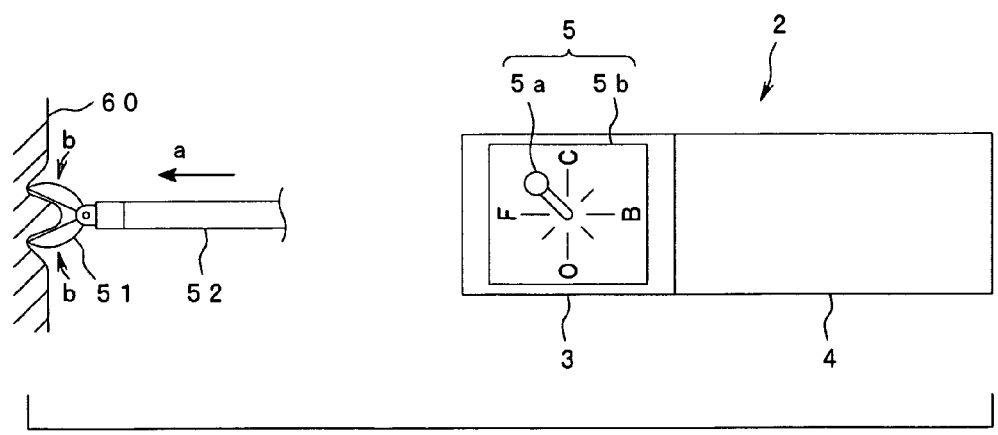
FIG. 11 is a diagram explaining a state where the biopsy forceps are operated by the operation instructing device.

For example, the operator tilts the control lever 5a on the operation instructing device 2 in the direction between the reference mark "FORWARD (F)" and that "CLOSE (C)" by a predetermined angle as shown in FIG. 11. Then, the tissue pickup member 51 is moved forward to the tissue 60 as shown by an arrow a and is also closed as shown by arrows b. In other words, when the operator tilts the control lever 5a in the direction between the reference mark "FORWARD (F)" and that "CLOSE (C)" as shown in the diagram, the tissue pickup member 51 is moved forward to the tissue and the tissue pickup member 51 is switched from the open state to the closed state to pick up the tissue 60.

After that, the operator tilts the control lever 5a toward the reference mark "BACKWARD (B)". Consequently, the tissue pickup member 51 with the picked tissue 60 is moved backward. Then, when the operator releases the tilting operation, the tissue pickup member 51 with the picked tissue 60 is arranged in a treatment position in front of the surface of the distal end portion 11a.

Figure 12:
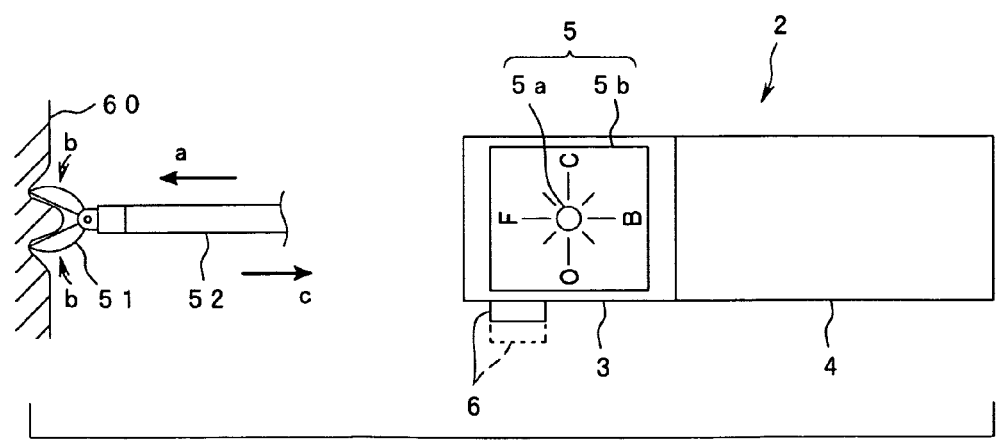
FIG. 12 is a diagram explaining a state where the biopsy forceps are operated in the programmed operation.

On the other hand, when the operator selects the program operation unit 6 which is located as shown by a broken line in FIG. 12 and pushes it as shown by a solid line, a second instruction signal is output to the CPU 21. The CPU 21 executes the biopsy-forceps operation program a on the basis of the accessory information previously output from the reader/writer 32c. Thus, the tissue pickup member 51 is moved forward, opened, closed, and moved backward in the operation based on the biopsy-forceps operation program.

Specifically, the biopsy-forceps operation program is executed in the state shown in FIG. 10 and the CPU 21 outputs various control signals to the motor-driven operating device 30 and the motor-driven forward/backward moving device 40.

Under the control of the CPU 21, the tissue pickup member 51 is moved forward toward the tissue 60 at a preset speed as shown by the arrow a. The tissue pickup member 51 continuously moved forward is pressed against the tissue 60. Then, the sensors 51a provided for the tissue pickup member 51 output a result of detection to the CPU 21.

The CPU 21 determines whether the detection result output from the sensors 51a reaches a predetermined set value. When the detection result reaches the set value, the CPU 21 controls to stop the forward movement of the tissue pickup member 51.

After that, under the control of the CPU 21, the tissue pickup member 51 is closed at a preset speed as shown by the arrows b. When the tissue pickup member 51 is completely closed, alternatively, when the amount of closing force detected by the sensors 51a reaches a preset value, the closing operation is stopped.

Subsequently, under the control of the CPU 21, the tissue pickup member 51 in the closed state is moved backward in the direction shown by an arrow c at a preset speed by a preset distance, thus picking up tissue. After that, the tissue pickup member 51 is moved backward in the direction shown by the arrow c at a preset speed by a preset distance. The programmed operation then terminates. In this instance, the tissue pickup member 51 holding the picked tissue 60 is positioned in front of the surface of the distal end portion 11a.

As mentioned above, the endoscopy system primarily includes the operation instructing device, the endoscope, the control device, the motor-driven operating device, and the motor-driven forward/backward moving device. The memory device in the control device stores the treatment operation programs, each of which enables the corresponding accessory attached to the motor-driven forward/backward moving device to perform predetermined treatment. The operation instructing device includes the manual operation instructing unit and the program operation instructing unit. Consequently, the operator can properly select the operation of an accessory attached to the motor-driven forward/backward moving device between the manual operation and the programmed operation. In other words, when the operator operates the control lever on the manual operation instructing unit, the treating member of the accessory is moved forward, opened, closed, and moved backward on the basis of the operation by the user's finger. On the other hand, when the operator operates the program operation instructing unit, the treating member of the accessory is moved forward, opened, closed, and moved backward in response to control signals output from the control device in the programmed operation. Advantageously, therefore, a doctor with little endoscopic surgery experience can operate an accessory to perform treatment in a manner similar to a doctor with rich endoscopic surgery experience.

During the programmed forward/backward moving operation and opening/closing operation, forward moving speed, backward moving speed, opening speed, closing speed, distance, and the amount of closing force may be changed by appropriately controlling an operation panel (not shown) provided for the control device. Thus, treatment can be performed at a speed desired by an operator.

According to the present embodiment, while the program operation unit 6 is being pushed in the position shown by the solid line, a first instruction signal is not output from the control lever 5a. In other words, the control lever 5a does not function. Therefore, even when the operator accidentally touches the control lever 5a during the programmed operation, the forward/backward moving operation or the opening/closing operation based on the program can be continued.

Further, according to the present embodiment, the pickup ring includes the IC chip 56, serving as accessory specifying means, and the protruding portion of the ring retainer includes the reader/writer 32c. However, the accessory specifying means is not limited to the above-described structure. A bar code and a bar code reader may be used. In this case, for example, a bar code is assigned to the pickup ring and a bar code reader is provided for the ring base so as to face a bar code.

According to the present embodiment, the memory device stores the treatment operation programs corresponding to a plurality of kinds of accessories. However, a memory card storing a treatment operation program may be prepared every accessory. In other words, each time an accessory is set, the corresponding memory card may be inserted into the control device to perform treatment.

In the above-described endoscopy system 1, the accessory is the biopsy forceps 50. However, the accessory is not limited to the biopsy forceps 50. Various accessories, e.g., a diathermic snare, a cannula, and basket forceps, can be operated in accordance with respective programs. Examples of programmed operations corresponding to other accessories attached to the motor-driven forward/backward moving device will be described below.

Examples of the programmed operations corresponding to the other accessories will now be described with reference to FIGS. 13A to 15B.

An example of the programmed operation of severing a lesion, such as a polyp, using a diathermic snare will now be described with reference to FIGS. 13A to 13C.

In the case of using a diathermic snare 50A as an accessory, a handle 53 thereof is also set to the motor-driven operating device 30. When the handle 53 is set to the motor-driven operating device 30, information stored in an IC chip 56 provided for the handle 53 is read by the reader/writer 32c and the read information is output to the CPU 21. In the diathermic snare 50A, a slider 55 constituting the handle 53 is moved forward or backward along the axis of the handle 53 in a manner similar to the above-described embodiment. In the diathermic snare 50A, forwardly moving the slider 55 projects a snare portion 51A from the distal end of a sheath 52, thus shaping the snare portion 51A into a loop. On the other hand, backwardly moving the slider 55 withdraws the loop-shaped snare portion 51A into the sheath 52.

The slider 55 of the diathermic snare 50A used in this embodiment includes a high-frequency cord (not shown). The high-frequency cord is connected to a high-frequency power supply (not shown). The high-frequency cord is connected to a metal operating wire (not shown) arranged in the sheath 52 through the slider 55 such that the cord is electrically connected to the snare portion 51A. The high-frequency power supply is connected to a foot switch (not shown). Therefore, when the operator appropriately operates the foot switch, a high frequency current is supplied to the snare portion 51A. In other words, while the base of a lesion is being tied by the snare portion 51A of the diathermic snare 50A, the foot switch is controlled to supply a high frequency current to the snare portion 51A, thus severing the lesion.

In the endoscopy system 1 in which the handle 53 of the diathermic snare 50A is mounted on the motor-driven operating device 30, the operator pushes the program operation unit 6 provided for the operation instructing device 2 to execute the diathermic-snare operation program.

Specifically, as shown in FIG. 13A, the operator operates the control lever 5a to insert a lesion 57a in the tissue 60 in the body cavity into the loop-shaped snare portion 51A. At that time, the operator pushes the program operation unit 6 provided for the operation instructing device 2.

Then, the CPU 21 executes the diathermic-snare operation program b in response to a second instruction signal output from the program operation unit 6. Thus, under the control of the CPU 21, as shown in FIG. 13B, the sheath 52 is moved forward in the direction shown by an arrow d at a preset speed. Simultaneously, the snare portion 51A is moved backward in the direction shown by an arrow e at the same speed such that the snare portion 51A is operatively associated with the sheath 52.

Thus, the snare portion 51A is withdrawn into the sheath 52 without slipping the lesion 57a from the loop-shaped snare portion 51A and the size of the loop is reduced. In other words, while the distal end of the snare portion 51A is held at a position shown by a broken line A, the operation of reducing the size of the loop is performed, thus preventing the lesion 57a from slipping from the snare portion 51A.

Each of the sheath 52 and the snare portion 51A is moved by a predetermined distance such that they are operatively associated with each other. After that, the programmed operation terminates. At that time, as shown in FIG. 13C, the size of the loop of the snare portion 51A is reduced to tie the base of the lesion 57a. The operator observes an endoscopic image displayed on the screen of the display and confirms the state of the tied lesion 57a. When properly done, the operator controls the foot switch (not shown) to supply a high frequency current to the snare portion 51A. Thus, the lesion 57a is severed from the tissue 60.

The following design may be used. When the program operation unit 6 is pushed, the sheath 52 and the snare portion 51A are continuously moved such that they are operatively associated with each other. When the program operation unit 6 is turned off, the sheath 52 and the snare portion 51A are stopped.

An example of the programmed operation of inserting a cannula into, e.g., a bile duct will now be explained with reference to FIGS. 14A and 14B.

In the case of using a cannula 50B as an accessory, a handle 53 thereof is also set to the motor-driven operating device 30. When the handle 53 is set to the motor-driven operating device 30, information stored in an IC chip 56 provided for the handle 53 is read by the reader/writer 32c and the read information is output to the CPU 21. In the cannula 50B, a slider 55 constituting the handle 53 is moved forward or backward along the axis of the handle 53 in a manner similar to the above-described embodiment. In the cannula 50B, when the slider 55 is moved forward or backward, a distal end portion 58a of an insertion section 58 is bent in either of two directions, i.e., upwardly or downwardly.

To find the position and type of a stone or an abnormal biliary function, the cannula 50B is used to inject a dye for endoscopic retrograde cholangiopancreatography into a bile duct 59a or a pancreatic duct 59b. A side view endoscope is used to insert the cannula 50B into the bile duct 59a. In this example, for convenience of explanation, components of the side view endoscope will be described using the same reference numerals as those assigned to the components of the above-described endoscope 10. In an operation instructing device 2A used in this embodiment, operating the slider 55 bends the distal end portion 58a. In a control-lever supporting portion 5b, therefore, a reference mark "FORWARD (F)" may be printed at the distal end of the control-lever supporting portion 5b, a reference mark "BACKWARD (B)" may be printed at the proximal end, a reference mark "UPWARD (U)" may be printed on the left, i.e., at the lower end in the diagram, and a reference mark "DOWNWARD (D)" may be printed on the right, i.e., at the upper end in the diagram.

In the endoscopy system 1 in which the handle 53 of the cannula 50B is mounted on the motor-driven operating device 30, the operator pushes a program operation unit 6 provided for the operation instructing device 2A, thus executing the cannula operation program c. In this instance, in the present embodiment, a control lever 5a serves as a selecting switch for selecting a "bile duct" or a "pancreatic duct".

Figure 14A:
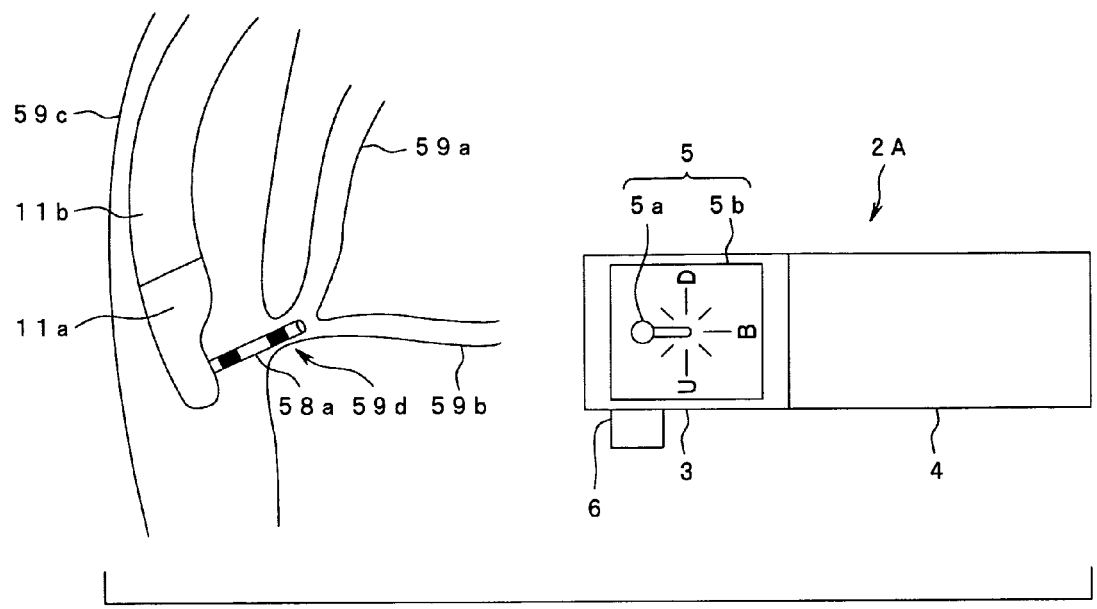
FIG. 14A is a diagram explaining a state where a cannula is introduced into a papillary region by operating the operation instructing device.
Figure 14B:
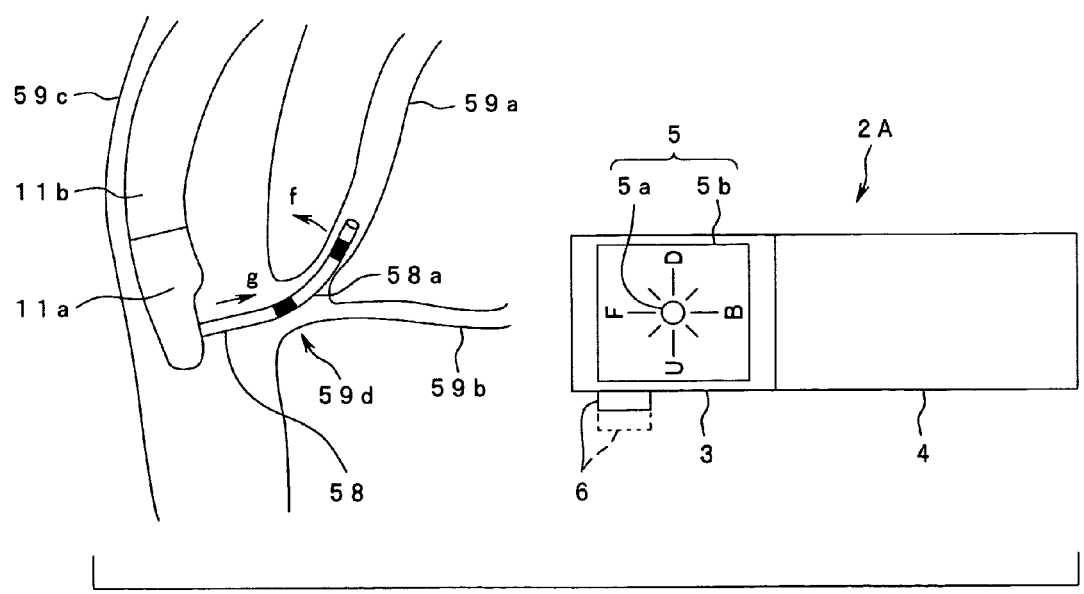
FIG. 14B is a diagram explaining a state where the cannula is introduced into a bile duct in the programmed operation.

Specifically, as shown in FIG. 14A, the operator first positions a distal end portion 11a of a side view endoscope 10 in the vicinity of a papillary region 59d of a duodenum 59c. After that, the operator operates the control lever 5a to project the cannula 50B from the distal end portion 11a. While observing endoscopic images, the operator inserts the cannula 50B into the papillary region 59d. In this instance, the operator pushes the program operation unit 6 provided for the operation instructing device 2A and simultaneously tilts the control lever 5a once toward substantially the reference mark "UPWARD (U)" with respect to the virtual line connecting the marks "FORWARD (F)" and "BACKWARD (B)".

Then, the CPU 21 executes the cannula operation program c in response to a second instruction signal output from the program operation unit 6 and a selection signal output from the control lever 5a. Thus, under the control of the CPU 21, as shown in FIG. 14B, while the distal end portion 58a is being bent in the direction shown by an arrow f by a preset amount, the insertion section 58 is projected in the direction shown by an arrow g at a preset speed.

After the insertion section 58 is projected at a predetermined amount, the programmed operation terminates. At that time, the distal end portion 58a of the cannula 50B is introduced in the bile duct 59a by a predetermined distance. After that, the operator injects the dye into the bile duct 59a through the cannula 50B.

When the cannula operation program c is executed to introduce the distal end portion 58a of the cannula 50B into the pancreatic duct 59b by a predetermined distance, the operator pushes the program operation unit 6 and tilts the control lever 5a once toward substantially the reference mark "DOWNWARD (D)".

As for the structure of the program, instead of the above-described operation setting in which the insertion section is bent and is then moved forward at the preset speed, the following operation setting may be used. The insertion section is slowly moved forward at a predetermined speed while slowly bending at a predetermined rate. When the program operation unit 6 is turned off, the insertion section is stopped.

An example of the programmed operation of retrieving, e.g., a gallstone using basket forceps will now be described with reference to FIGS. 15A and 15B.

In the case of using basket forceps 50C as an accessory, a handle 53 thereof is also set to the motor-driven operating device 30. When the handle 53 is set to the motor-driven operating device 30, information stored in an IC chip 56 provided for the handle 53 is read by the reader/writer 32c and the read information is output to the CPU 21. In the basket forceps 50C, a slider 55 constituting the handle 53 is moved forward or backward along the axis of the handle 53 in a manner similar to the above-described embodiment. In the basket forceps 50C, forwardly or backwardly moving the slider 55 switches a retrieval basket 51C between an open state and a retrieval state.

An endoscope used in inserting the basket forceps 50C into the bile duct 59a is a side view endoscope in the same case as the above-described embodiment. As for the operation instructing device 2 used in this embodiment, since the retrieval basket 51C is switched between the open state and the retrieval state, i.e., a closed state by operating the slider 55, the operation instructing device 2 is used.

In the endoscopy system 1 in which the handle 53 of the basket forceps 50C is set in the motor-driven operating device 30, the operator pushes the program operation unit 6 provided for the operation instructing device 2, thus executing the basket-forceps operation program d. At that time, in this embodiment, the control lever 5a does not function as the control lever 5a nor function as the selecting switch.

Figure 15A:
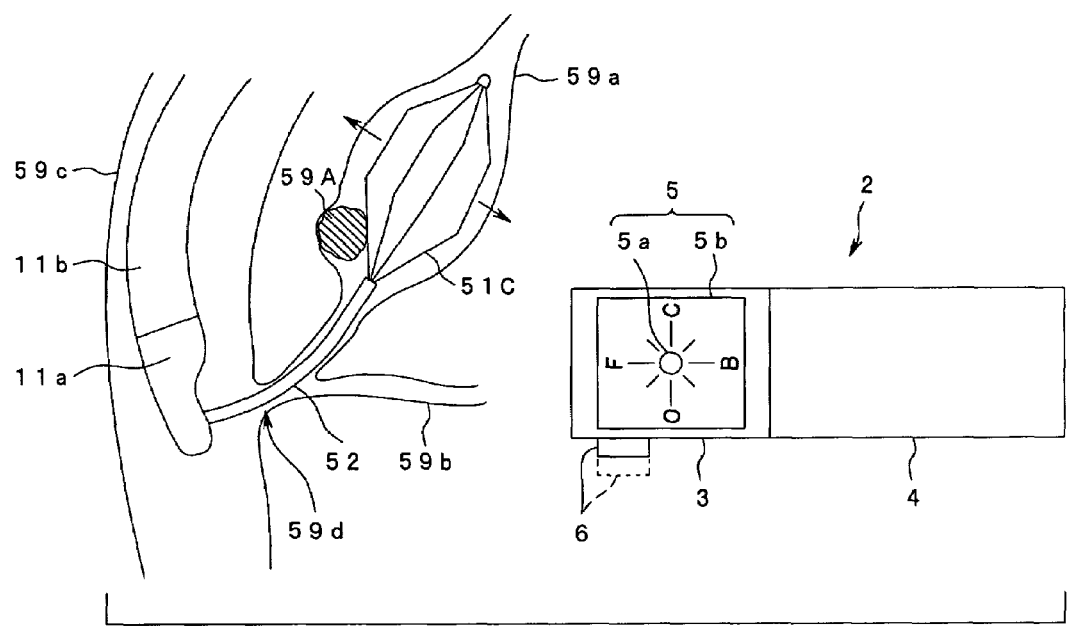
FIG. 15A is a diagram explaining a state where a retrieval basket of basket forceps is developed by operating the operation instructing device.
Figure 15B:
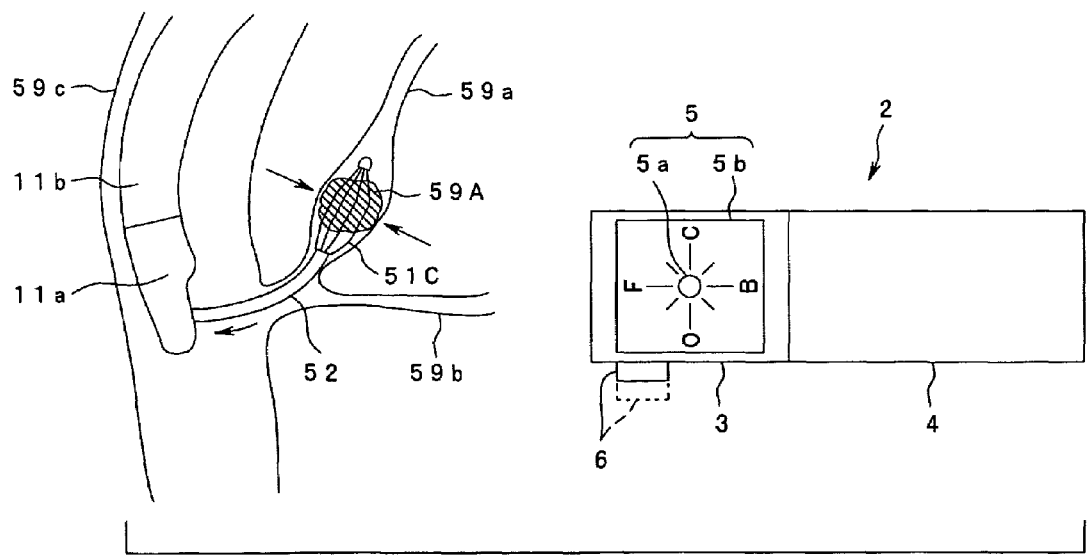
FIG. 15B is a diagram explaining a state where a gallstone is retrieved and held by the retrieval basket in the programmed operation.

Specifically, as shown in FIG. 15A, the operator first positions the distal end portion 11a of the side view endoscope 10 in the vicinity of the papillary region 59d of the duodenum 59c. After that, while observing an endoscopic image, the operator introduces a sheath 52 of the basket forceps 50C into the bile duct 59a. Then, the operator projects the retrieval basket 51C from the sheath 52 and develops it into the open state in the bile duct 59a as shown by arrows. At that time, the operator pushes the program operation unit 6 provided for the operation instructing device 2.

The CPU 21 executes the basket-forceps operation program d in response to a second instruction signal output from the program operation unit 6. Consequently, under the control of the CPU 21, the retrieval basket 51C is opened and closed, so that the spacing of wires constituting the retrieval basket 51C is widened and narrowed. Therefore, the positions and orientations of the wires constituting the retrieval basket 51C are changed relative to a stone 59A, thus putting the stone 59A into the retrieval basket 51C. As shown in FIG. 15B, while the retrieval basket 51C is being closed, the sheath 52 is moved backward. In other words, while the retrieval basket 51C is withdrawn into the sheath 52 at a preset rate, the sheath 52 is moved backward at a preset rate. When the program operation unit 6 is turned off, the movement is stopped.

Consequently, the stone 59A is held in the retrieval basket 51C. The programmed operation terminates. In this instance, the removed retrieval basket 51C with the retrieved stone 59A out of the bile duct 59a is observed through an observation window (not shown) provided for the distal end portion 11a.

Figure 16:
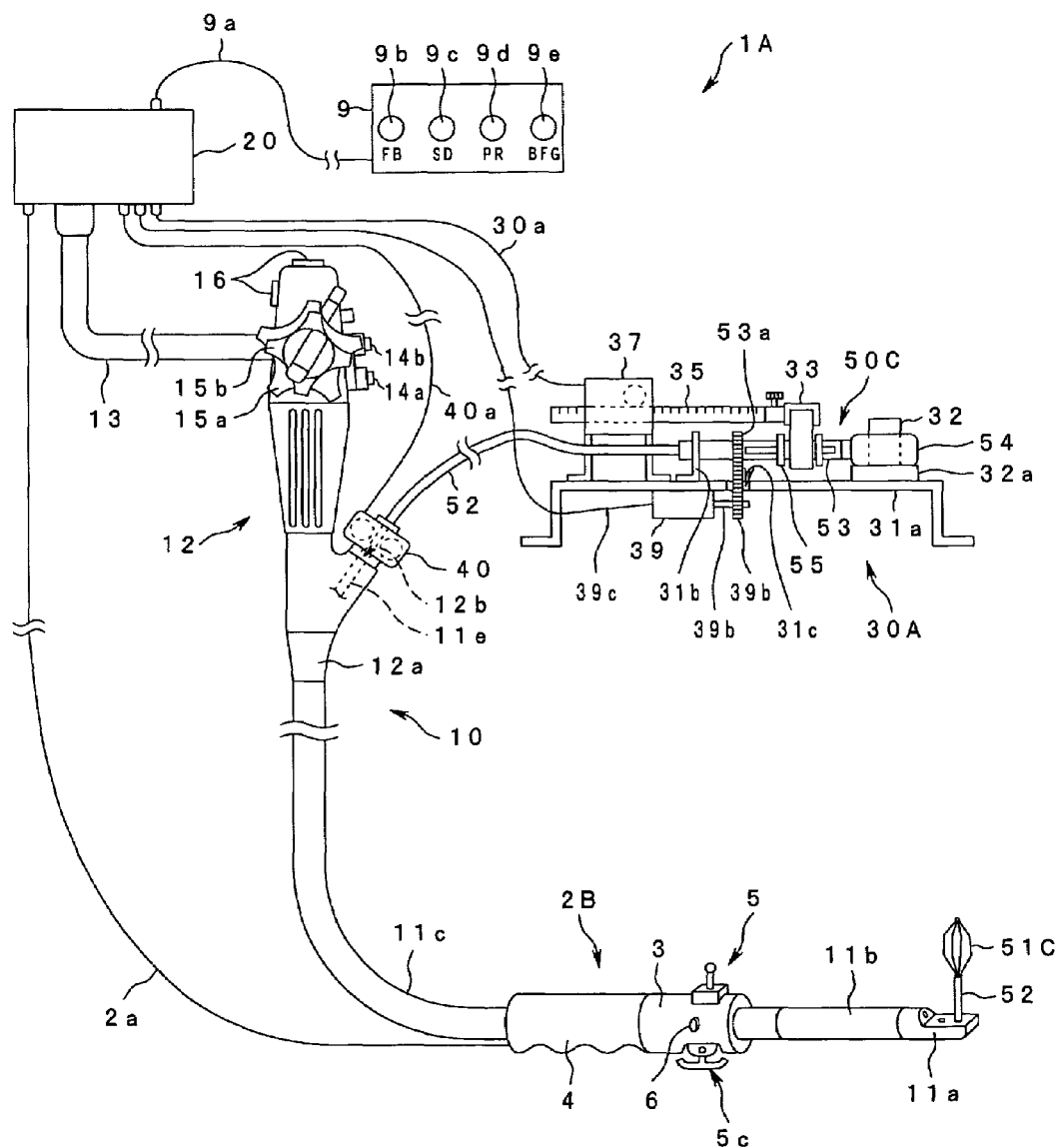
FIG. 16 is a diagram explaining the entire structure of an endoscopy system according to a second embodiment.

A second embodiment of the present invention will now be described with reference to FIGS. 16 to 17B.

An endoscopy system 1A shown in FIG. 16 includes an accessory specifying device (hereinafter, referred to as a selector) 9, serving as accessory specifying means. A motor-driven operating device 30A includes a rotary motor 39 for rotating the distal end of the handle 53 of the basket forceps 50C about the long axis of the sheath 52.

A torque transmission gear (hereinbelow, referred to as a gear) 39b, serving as a spur gear, is attached to a motor shaft 39a of the rotary motor 39. The rotary motor 39 is electrically connected to a control device 20 via an electric cable 39c. The rotary motor 39 is fixed to the rear surface of a base 31a shaped substantially like a hat.

The base 31a has a hole 31c in which the gear 39b of the rotary motor 39 is exposed. In stead of the mount 38, the base 31a has a rotation holding member (hereinafter, referred to as a holding member) 31b for rotatably holding the distal end part of the handle 53. A driven gear 53a meshing with the gear 39b is arranged in the distal end part of the handle 53 of the basket forceps 50C.

In an operation instructing device 2B according to the present embodiment, a rotation instructing unit 5c is arranged on the side surface of the operation instructing device 2B such that the rotation instructing unit 5c and a manual operation unit 5 on a body portion 3 are arranged on opposite sides. A program operation unit 6 is arranged on, e.g., the right relative to the distal end of the operation instructing device 2B as viewed from above such that the position of the unit 6 is deviated from that of the manual operation unit 5 in the circumferential direction by 90 degrees. In addition, the operation instructing device 2B is attached to a flexible tube 11c. Therefore, an operator can operate the program operation unit 6 while grasping the flexible tube 11c.

The rotation instructing unit 5c functions as a switch for selecting between driving and non-driving modes of the rotary motor 39. When the rotation instructing unit 5c is perpendicular to the longitudinal axis of the operation instructing device 2B, the rotation instructing unit 5c is in the OFF state. The rotation instructing unit 5c can be tilted from an initial position in the OFF state toward the distal end or the proximal end. When the rotation instructing unit 5c is tilted, a rotation instruction signal is output to the control device 20 via a signal cable 2a extending from a grip member 4. When the rotation instructing unit 5c is tilted toward the distal end, the retrieval basket 51C is rotated counterclockwise with respect to the direction from the proximal end thereof to the distal end. On the other hand, when the rotation instructing unit 5c is tilted toward the proximal end, the retrieval basket 51C is rotated clockwise with respect to the direction from the proximal end thereof to the distal end.

In other words, as described in the foregoing first embodiment, an operator can switch the retrieval basket 51C between the open state and the retrieval state by operating a control lever 5a using their thumb or the like. In addition, the operator can rotate the retrieval basket 51C about the axis by operating the rotation instructing unit 5c using their index finger or the like.

According to the present embodiment, changing the angle of tilt of the rotation instructing unit 5c varies rotating speed. In other words, the larger the angle of tilt of the rotation instructing unit 5c is, the faster the rotating speed is.

The selector 9 is electrically connected to the control device 20 through a signal cable 9a. The selector 9 includes a plurality of accessory specifying units (hereinafter, referred to as buttons) 9b, 9c, 9d, . . . For example, when the operator pushes the button 9b corresponding to an accessory mounted on the motor-driven operating device 30A, accessory information is output to the control device 20.

In the vicinity of the respective buttons 9b, 9c, and 9d, e.g., on the lower side of the buttons, illustrations, characters, or symbols indicative of the kinds of accessories are printed. According to the present embodiment, symbols are used. Symbols "FB", "SD", "PR", and "BFG" indicate biopsy forceps, a diathermic snare, a cannula, and basket forceps, respectively. In addition to the above buttons, the selector 9 includes a button for grasping forceps, shown by a symbol "FG", a button for a balloon catheter, shown by a symbol "B", and a button for a diathermic knife, shown by a symbol "KD".

The other structure of the endoscopy system 1A is the same as that of the endoscopy system 1 according to the first embodiment. The same components as those of the endoscopy system 1 are designated by the same reference numerals and a description of the same components is omitted. According to the present embodiment, the accessory is the basket forceps 50C. An accessory used in the present system 1A is not limited to the basket forceps 50C. An endoscope 10 according to the present embodiment is a side view endoscope described above.

The operation of the endoscopy system 1A with the above-described structure will now be explained.

After completion of preparation, a medical staff turns on the control device 20 and pushes one of the buttons 9b, 9c, 9d, . . . arranged in the selector 9, the pushed button corresponding to an accessory mounted on the motor-driven operating device 30A. In this present embodiment, since the accessory is the basket forceps, the operator pushes the corresponding button 9e. Then, accessory information indicating that the accessory is the basket forceps is output to a CPU 21.

Subsequently, the operator inserts an insertion section 11 of the endoscope 10 into the body cavity of a subject to a target region while observing endoscopic images. Then, the operator performs the inserting operation and the bending operation of bending a bendable portion 11b while confirming endoscopic images on a screen, thus allowing a distal end portion 11a of the insertion section 11 to face a papillary region 59d so as to easily perform treatment.

After that, the operator holds the operation instructing device 2B in order to operate the basket forceps 50C while observing endoscopic images.

In this instance, the operator operates the control lever 5a of the manual operation unit 5 to position the sheath 52 and the retrieval basket 51C in a bile duct 59a. In other words, the operator projects the sheath 52 from the distal end portion 11a of the insertion section 11 of the endoscope 10 inserted into a duodenum 59c to insert the sheath 52 into the bile duct 59a in a manner similar to the above-described operation shown in FIG. 15A, and develops the retrieval basket 51C as shown in FIG. 17A.

In this state, the operator operates the control lever 5a and the rotation instructing unit 5c in order to retrieve a stone.

Figure 17A:
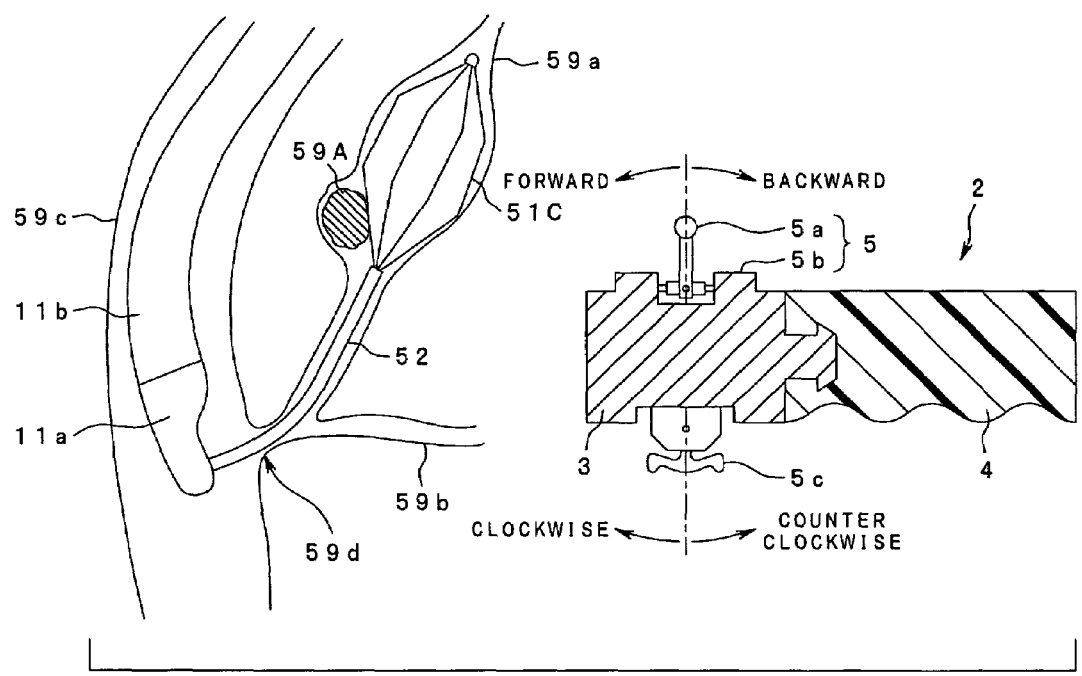
FIG. 17A is a diagram explaining a state where the retrieval basket of the basket forceps is developed by operating an operation instructing device.
Figure 17B:
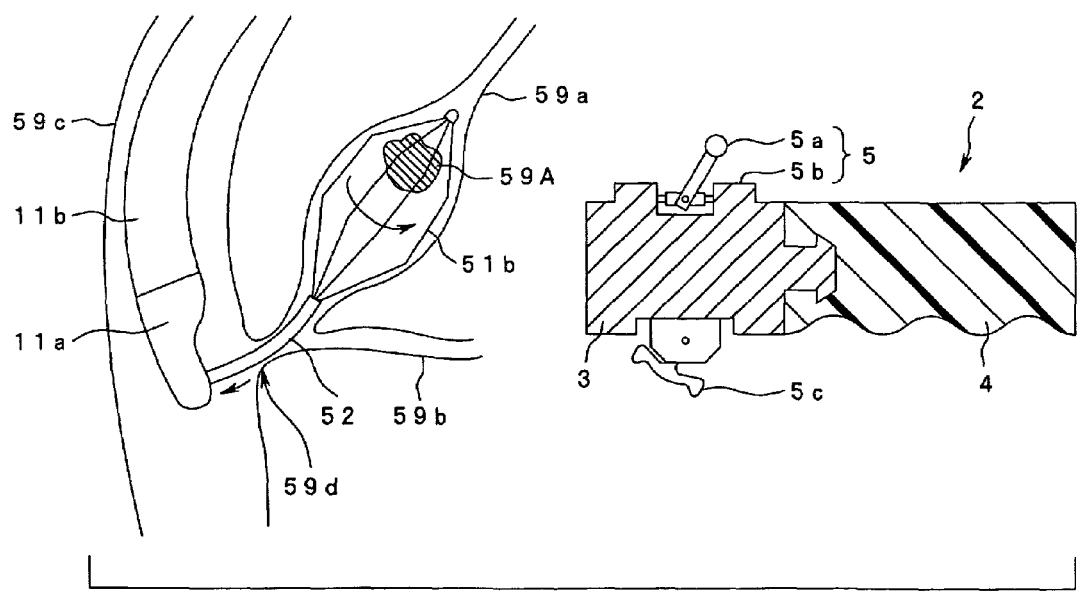
FIG. 17B is a diagram explaining a state where the retrieval basket of the basket forceps is rotated to retrieve a gallstone by operating the operation instructing device.

Specifically, as shown in FIG. 17B, the operator tilts the control lever 5a of the manual operation unit 5 toward, e.g., the proximal end to move the sheath 52 backward, and simultaneously tilts the rotation instructing unit 5c toward, e.g., the distal end to rotate the retrieval basket 51C clockwise. Then, a stone 59A in the bile duct 59a is captured into the rotating retrieval basket 51C. Substantially simultaneously with the rotation, the operator tilts the control lever 5a of the manual operation unit 5 toward a reference mark "CLOSE (C)". Thus, the retrieval basket 51C is contracted to hold the stone 59A. The retrieval basket 51C holding the stone 59A can be removed out of the bile duct 59a.

Figure 18:
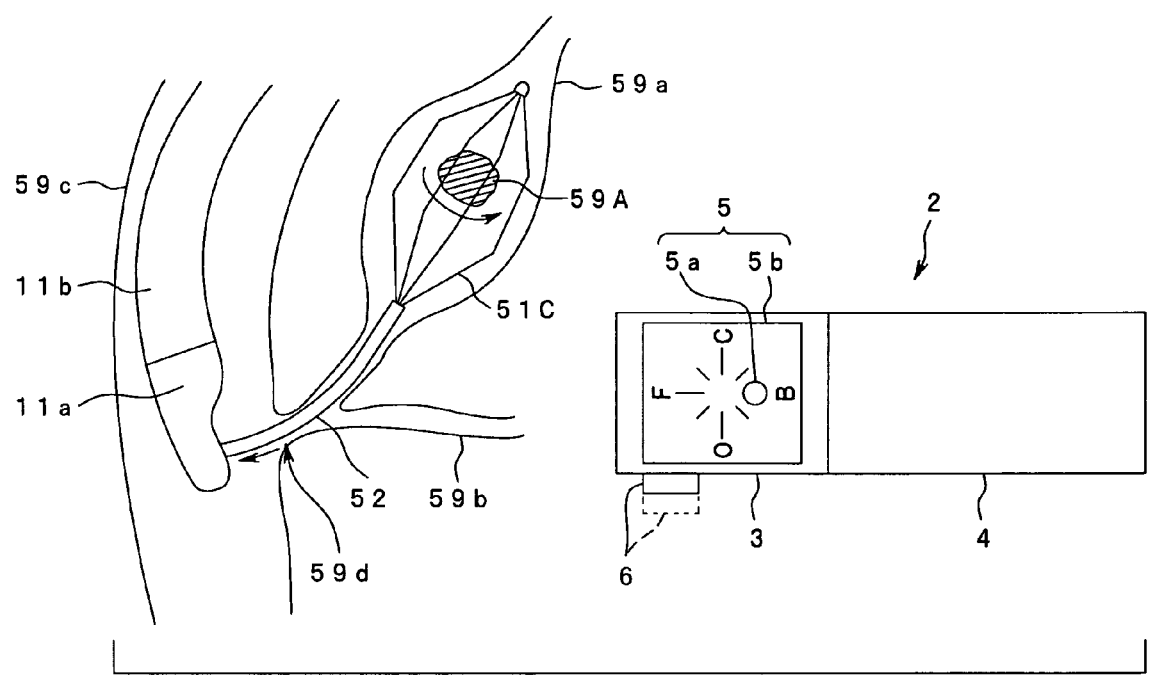
FIG. 18 is a diagram explaining a state where the retrieval basket of the basket forceps is rotated to retrieve a gallstone in the programmed operation.

On the other hand, when the operator pushes the program operation unit 6, located in a position shown by a broken line in FIG. 18, to a position shown by a solid line while the retrieval basket 51C is being developed as shown in FIG. 17A, the operation enters a programmed mode. In this instance, in the present embodiment, the control lever 5a may function as a selecting switch for selecting between a "treating-member rotation unwanted mode", and a "treating-member rotation wanted mode".

In the case of using the lever as the selecting switch, the treating-member rotation unwanted mode is selected by tilting the control lever 5a toward, e.g., the distal end. In this case, as explained with reference to FIGS. 15A and 15B, the retrieval basket 51C is not rotated. While the retrieval basket 51C is being closed, the sheath 52 is moved backward to retrieve a gallstone. In other words, a gallstone is retrieved without using the rotary motor 39. On the other hand, when the control lever 5a is tilted toward the proximal end, the treating-member rotation wanted mode is selected. In this case, the rotary motor 39 is used to rotate the retrieval basket 51C as described above, thus retrieving a gallstone. When the lever is not set as the selecting switch, the retrieval basket 51C is always set so as to rotate.

As for the rotation instructing unit 5c, when the program operation unit 6 is pushed, the rotation instructing unit 5c may function as the selecting switch for selecting the rotating direction. When the unit 5c is not allowed to function as the selecting switch, the retrieval basket 51C is always rotated, e.g., clockwise.

When the control lever 5a is tilted to the proximal end after the pushing of the program operation unit 6, the program for rotating the treating member is executed. Then, under the control of the CPU 21, while the retrieval basket 51C is being rotated, the sheath 52 is moved backward. In this instance, each of a rotating speed and a backward moving speed is set to a preset speed. Thus, the stone 59A is captured into the retrieval basket 51C. As for the structure of the program, three actions, i.e., the rotation of the retrieval basket 51C, the rotation of the sheath 52, and the closing of the basket 51C may be simultaneously performed such that the three actions are operatively associated with each other.

As mentioned above, the endoscopy system includes the selector having the buttons each of which outputs accessory information. Thus, when the operator operates any button provided for the selector, accessory information can be output to the control device. Advantageously, it is unnecessary to provide an IC chip for each accessory.

In addition, the motor-driven operating device includes the rotary motor for rotating a treating member and the operation instructing device includes the rotation instructing unit for selecting whether the rotary motor is driven. Advantageously, therefore, treatment can be performed while a treating member is being rotated as necessary.

Further, a memory device of the control device is allowed to store treatment operation programs corresponding to accessories to be mounted on the motor-driven forward/backward moving device, each program allowing the corresponding accessory to perform predetermined treatment. In addition, the manual operation instructing unit and the program operation instructing unit are provided for the operation instructing device. When the program operation instructing unit is selected, the manual operation instructing unit serves as the switch for selecting whether the treating member is rotated using the rotary motor.

Consequently, the operator operates the program operation instructing unit and then operates the manual operation instructing unit, thus selecting whether treatment is performed while the treating member of the accessory is being rotated.

Figure 19:
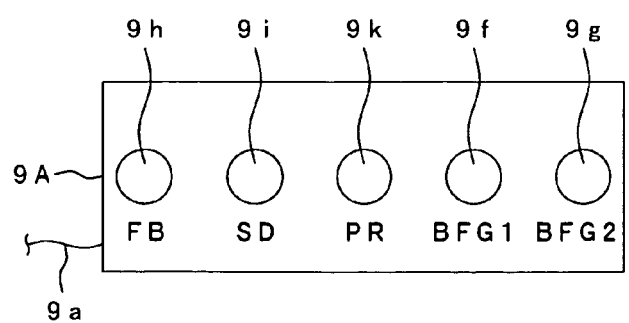
FIG. 19 is a diagram explaining an example of another structure of a selector.

According to the present embodiment, after the program operation unit is pushed, the control lever is operated in a predetermined direction, thus rotating the retrieval basket. However, as shown in FIG. 19, a program operation button 9f for outputting an instruction signal to execute the basket-forceps operation program without rotating the retrieval basket and a program operation button 9g for outputting an instruction signal to execute the basket-forceps operation program while rotating the retrieval basket may be provided for a selector 9A.

In other words, operating either of the above buttons outputs accessory information and a second instruction signal. Thus, the program operation unit 6 can be omitted in the operation instructing device 2B and an operation program corresponding to an accessory can be executed. In the selector 9A shown in FIG. 19, a program operation button 9h outputs an instruction signal to execute the biopsy-forceps operation program and accessory information indicating that the accessory is biopsy forceps. A program operation button 9i is used for the diathermic-snare operation program and a program operation button 9k is used for the cannula operation program. Each button outputs an instruction signal to execute the corresponding program and accessory information.

Figure 20:
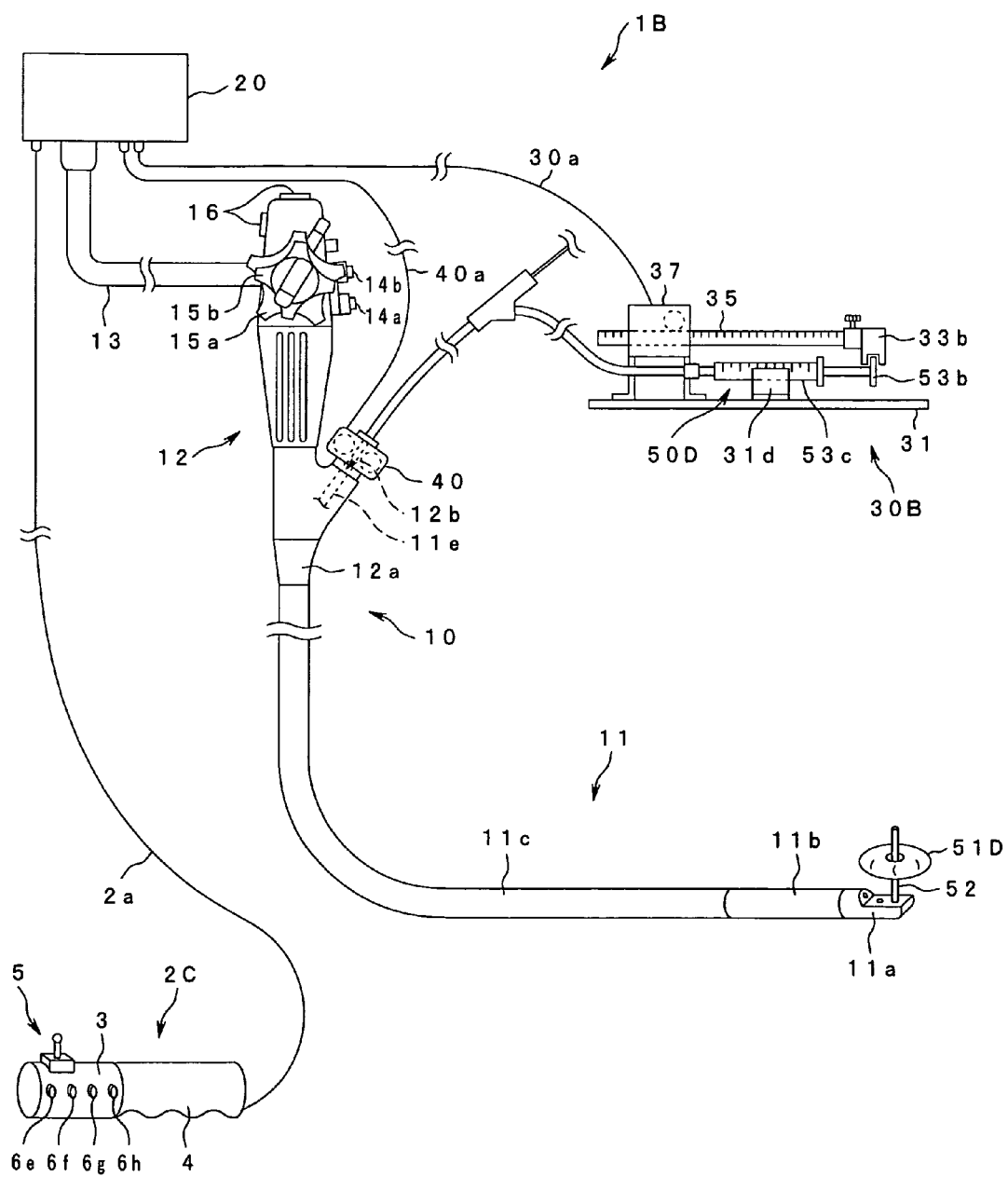
FIG. 20 is a diagram explaining the entire structure of an endoscopy system according to a third embodiment.
Figure 21:
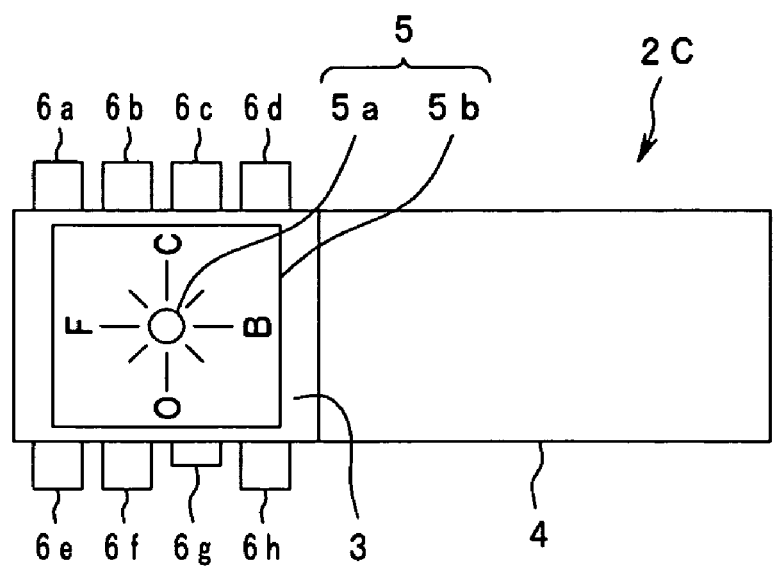
FIG. 21 is a diagram explaining an operation instructing device including a plurality of program operation units.

As shown in FIGS. 20 and 21, the selector 9 may be omitted and an operation instructing device 2C may include a plurality of program operation units 6a, 6b, 6c, . . . , each of which outputs accessory information about the corresponding accessory and a second instruction signal. In other words, each program operation unit also serves as an accessory specifying unit. Thus, when the program operation unit 6a is selected on the operation instructing device 2C, the corresponding accessory can be controlled in the programmed operation. The program operation unit 6a corresponds to biopsy forceps, the program operation unit 6b corresponds to a diathermic snare, the program operation unit 6c corresponds to a cannula, the program operation unit 6d corresponds to basket forceps in the rotation unwanted mode, the program operation unit 6e corresponds to that in the rotation wanted mode, the program operation unit 6f corresponds to grasping forceps, the program operation unit 6g corresponds to a balloon catheter, and the program operation unit 6h corresponds to a diathermic knife. In the vicinity of the respective program operation units 6a, 6b, 6c, . . . , illustrations, characters, or symbols indicative of the kinds of accessories are arranged.

In an endoscopy system 1B shown in FIG. 20, a syringe 50D for inflating or deflating a balloon 51D of the balloon catheter is mounted on a motor-driven operating device 30B. The specifications of the motor-driven operating device 30B are partially different from those of the above-described motor-driven operating device 30 in order to operate the syringe 50D. Specifically, in a base 31, a fixing member 31d is arranged instead of the mount 38 and the ring retainer 32 is not needed. A cylinder portion 53c of the syringe 50D is mounted on the fixing member 31d. Instead of the slider retainer 33 having the holding member 33a, a piston holding member 33b is attached to a rack 35. The piston holding member 33b holds the end portion of a piston 53b of the syringe 50D.

The other structure of the endoscopy system 1B is the same as that according to the foregoing first embodiment. The same components as those in the first embodiment are designated by the same reference numerals. A description of the same components is omitted.

The operation of the endoscopy system 1B with the above-described structure will now be explained.

After completion of preparation, a medical staff turns on a control device 20. An operator inserts an insertion section 11 of an endoscope 10 into the body cavity of a subject toward a target region while observing endoscopic images. The operator performs the inserting operation and the bending operation of bending a bendable portion 11b while confirming endoscopic images on a screen and allows a distal end portion 11a of the insertion section 11 to face a papillary region 59d so as to easily perform treatment.

After that, the operator holds the operation instructing device 2C in order to introduce a sheath 52 including the balloon 51D at the distal end into a bile duct 59a while observing endoscopic images, the balloon 51D being deflated.

Figure 22:
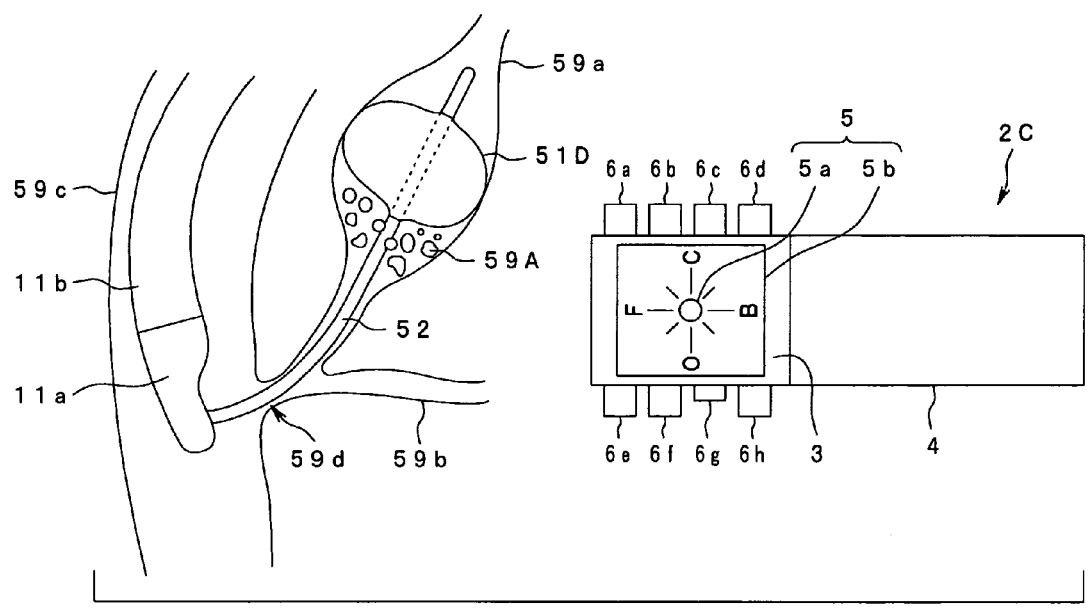
FIG. 22 is a diagram explaining a state where a balloon of a balloon catheter is inflated in the programmed operation.

At that time, the operator operates a control lever 5a of a manual operation unit 5 to position the sheath 52 in the bile duct 59a. Then, the operator projects the sheath 52 from the distal end portion 11a of the insertion section 11 of the endoscope 10 inserted into a duodenum 59c, thus inserting the sheath 52 into the bile duct 59a. In this state, the operator pushes the balloon-catheter program operation unit 6g in order to retrieve small stones 59A which are difficult to retrieve. Consequently, accessory information and a second instruction signal are output to the control device 20, thus executing a balloon-catheter program stored in a memory device 22 of the control device 20. Under the control of a CPU 21, the piston 53b is moved forward at a predetermined speed. As shown in FIG. 22, the balloon 51D is inflated at a predetermined rate of inflation until the internal pressure reaches a predetermined value.

Figure 23:
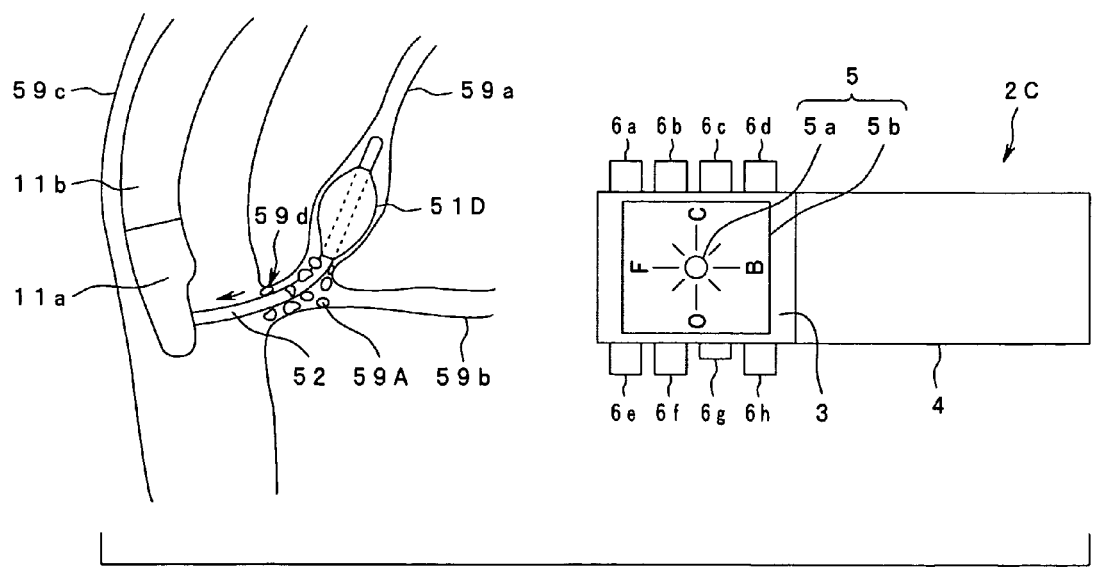
FIG. 23 is a diagram explaining a constant state where small gallstones are removed from a bile duct in the programmed operation, the diagram explaining the state where the balloon of the balloon catheter is inflated.

Subsequently, under the control of the CPU 21, the piston 53b is moved backward at a predetermined speed. As shown in FIG. 23, while the balloon 51D is being deflated, the sheath 52 is moved backward by a predetermined distance. Consequently, the small stones 59A in the bile duct 59a are removed from the bile duct 59a by the balloon 51D which is moved backward while being gradually deflated and are then introduced to the duodenum 59c.

As described above, the operation instructing device includes the program operation units corresponding to the plurality of kinds of accessories, each program operation unit outputting accessory information and a second instruction signal. When the operator intends to perform the programmed operation of a treating member of a desired accessory, the operator operates a program operation unit corresponding to the desired accessory. Consequently, a desired program stored in the memory device of the control device is executed, thus performing treatment.

Figure 24A:
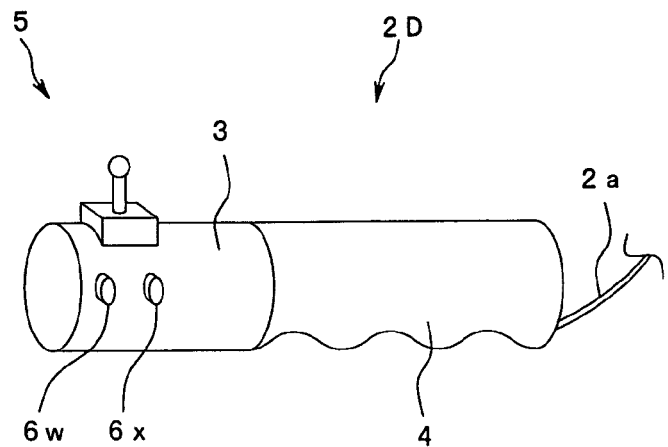
FIG. 24A is a diagram explaining an operation instructing device dedicated for the retrieval basket.
Figure 24B:
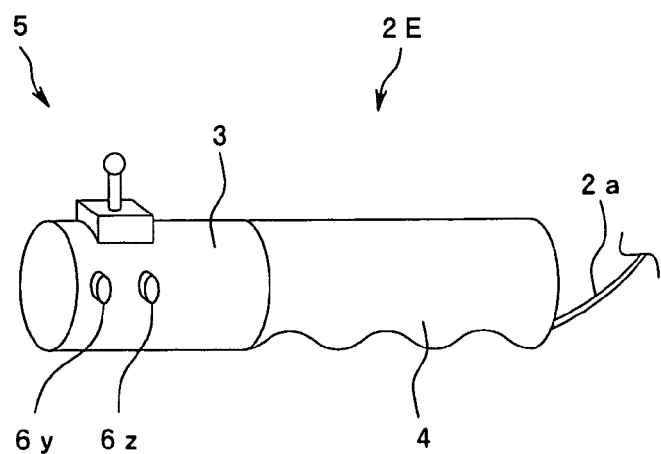
FIG. 24B is a diagram explaining an operation instructing device dedicated for a cannula.

In the above-described embodiment, all of accessories can be controlled using one operation instructing device. In other words, an operation instructing device dedicated for each accessory is not provided. As shown in FIG. 24A and 24B, an operation instructing device dedicated for each accessory may be provided.

FIG. 24A shows an operation instructing device 2D for a retrieval basket. In the operation instructing device 2D, a signal cable 2a thereof is connected to the above-described control device 20 to output accessory information to the CPU 21.

The operation instructing device 2D includes a manual operation unit 5 and two program operation units 6w and 6x each of which outputs a second instruction signal. When the program operation unit 6w is pushed, a second instruction signal to retrieve a gallstone without rotating a retrieval basket 51C is output to the control device 20. On the other hand, when the program operation unit 6x is pushed, a second instruction signal to retrieve a gallstone while rotating the retrieval basket 51C is output.

FIG. 24B shows an operation instructing device 2E for a cannula. When a program operation unit 6y is pushed, a second instruction signal to move the cannula forward and simultaneously bend it upward is output to the control device. On the other hand, when a program operation unit 6z is pushed, a second instruction signal to move the cannula forward and simultaneously bend it downward is output.

In this structure, the program operation unit corresponding to the desired operation for treatment can be easily selected. In the diagrams, the two program operation units are arranged in parallel to each other on one side. Alternatively, one program operation unit may be arranged on each side. Thus, the selection of any program operation unit can be performed with more reliability.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscopy system comprising:
    an operating device that an operation section of an accessory is attachable to, the operating device operating the operation section in a motor-driven manner, the accessory having an accessory insertion section to be introduced into a body cavity through an insertion section of an endoscope;
    a forward/backward moving device arranged in an operation section of the endoscope, the forward/backward moving device moving the accessory insertion section forward or backward in a motor-driven manner;
    a control device electrically connected to the forward/backward moving device and the operating device, the control device including a control unit for outputting control signals to the forward/backward moving device and the operating device and a memory unit for storing one or more treatment operation programs corresponding to accessories to be mounted on the operating device; and
    an operation instructing device electrically connected to the control device, the operation instructing device including a manual operation unit, a first operation instructing unit for outputting a first instruction signal corresponding to the operation of the manual operation unit, and a second operation instructing unit for outputting a second instruction signal, wherein
    when receiving the first instruction signal, the control device outputs a control signal corresponding to the first instruction signal to at least one of the forward/backward moving device and the operating device, and when receiving the second instruction signal, the control device executes the treatment operation program stored in the memory unit and then outputs a control signal, based on the operation according to the treatment operation program, to at least one of the forward/backward moving device and the operating device.

2. The endoscopy system according to claim 1, further comprising:

accessory specifying means electrically connected to the control device, the means outputting accessory information to specify the kind of accessory mounted on the operating device to the control device.

3. The endoscopy system according to claim 2, wherein the accessory specifying means includes:

an accessory information unit provided for each accessory, the unit storing accessory information to specify the kind of the accessory; and an information reading unit for reading information stored in the accessory information unit and outputting the result of reading as the accessory information to the control device.

4. The endoscopy system according to claim 2, wherein the accessory specifying means includes an accessory specifying device having an accessory specifying unit for outputting accessory information to selectively specify an accessory mounted on the operating device from a plurality of accessories.

5. The endoscopy system according to claim 4, wherein the accessory specifying unit of the accessory specifying device outputs the accessory information and the second instruction signal.

6. The endoscopy system according to claim 2, wherein the accessory specifying means includes an accessory specifying unit provided for the operation instructing device, the accessory specifying unit selectively specifying an accessory mounted on the operation device from among a plurality of accessories.

7. The endoscopy system according to claim 6, wherein the accessory specifying unit, provided for the operation instructing device, also functions as the second operation instructing unit.

* * * * *